(12) United States Patent
Kondo et al.

(10) Patent No.: US 8,772,475 B2
(45) Date of Patent: Jul. 8, 2014

(54) AZA COMPOUNDS AND PRODUCTION METHOD THEREOF, AND METAL COMPLEXES AS MRI CONTRAST AGENTS

(75) Inventors: Teruyuki Kondo, Kyoto (JP); Hiroshi Tsujita, Sakai (JP); Zainul Abedin Siddique, Chandgaon (JP); Shingo Matsuki, Toda (JP); Hiroki Miura, Kyoto (JP); Hidehito Tochio, Muko (JP); Tetsuya Matsuda, Kyoto (JP); Michiko Narazaki, Hirakata (JP); Hidetoshi Tsuzuki, Kawasaki (JP); Katsuaki Kuge, Yokohama (JP); Yoshinori Tomida, Atsugi (JP); Kimihiro Yoshimura, Yokohama (JP); Tetsuya Yano, Tsukuba (JP)

(73) Assignee: Canon Kabushiki Kaisha, Tokyo (JP)

( * ) Notice: Subject to any disclaimer, the term of this patent is extended or adjusted under 35 U.S.C. 154(b) by 328 days.

(21) Appl. No.: 12/743,777

(22) PCT Filed: Nov. 28, 2008

(86) PCT No.: PCT/JP2008/072113
§ 371 (c)(1),
(2), (4) Date: Sep. 8, 2010

(87) PCT Pub. No.: WO2009/069833
PCT Pub. Date: Jun. 4, 2009

(65) Prior Publication Data
US 2011/0028713 A1    Feb. 3, 2011

(30) Foreign Application Priority Data

Nov. 29, 2007 (JP) .................................. 2007-309087
Feb. 22, 2008 (JP) .................................. 2008-040990

(51) Int. Cl.
*C07D 225/00* (2006.01)

(52) U.S. Cl.
USPC ....................................................... 540/465

(58) Field of Classification Search
USPC ......................................................... 540/465
See application file for complete search history.

(56) References Cited

U.S. PATENT DOCUMENTS

| | | | |
|---|---|---|---|
| 5,695,739 A | 12/1997 | Schmitt-Willich et al. |
| 5,798,092 A | 8/1998 | Schmitt-Willich et al. |
| 6,039,931 A | 3/2000 | Schmitt-Willich et al. |
| 6,149,890 A | 11/2000 | Uggeri et al. |
| 6,177,562 B1 | 1/2001 | Uggeri et al. |
| 2010/0247444 A1 | 9/2010 | Yoshimura et al. |
| 2010/0248279 A1 | 9/2010 | Yamauchi et al. |

FOREIGN PATENT DOCUMENTS

EP    0 872 479 A1    10/1998

OTHER PUBLICATIONS

T. J. Atkins et al., "Macrocyclic Polyamines: 1,4,7,10,13,16-Hexaäzacyclooctadecane," Organic Syntheses, vol. 58, p. 86 (1978).
Bianchi Antonio et al., "Dicopper(II) Complex of the Large Polyazacycloalkane 1,4,7,10,13,16,19,22-Octaazacyclotetracosane (bistrien). Synthesis, Crystal Structure, Electrochemistry, and Thermodynamics of Formation," Inorg. Chem. 1985, 24, 1182-1187.
Han-Ting Chang et al., "Asymmetric Dihydroxylation Enables Rapid Construction of Chiral Dendrimers Based on 1,2-Diols," 35 Angew. Chem. Int. Ed. Engl. 182-186 (1996).

*Primary Examiner* — Brian McDowell
(74) *Attorney, Agent, or Firm* — Fitzpatrick, Cella, Harper & Scinto

(57) ABSTRACT

A core of a cyclic structure represented by $(-N-(CH_2)_n-)_k$ is bonded to a dendrimer-type side chain with a specific branched structure at all nitrogen atoms in the core to produce a compound with a specific structure for producing a metal complex that exhibits a T1-reducing effect, and the resulting compound is coordinated to a metal ion that has a T1-reducing effect to obtain a metal complex that exhibits an excellent T1-reducing effect which is useful as an effective component of an MRI contrast agent and an MRI contrast agent using the same.

3 Claims, 5 Drawing Sheets

AZA COMPOUNDS AND PRODUCTION METHOD THEREOF, AND METAL COMPLEXES AS MRI CONTRAST AGENTS

TECHNICAL FIELD

The present invention relates to a compound and a production method thereof, a metal complex and a production method thereof, and an MRI contrast agent.

BACKGROUND ART

Magnetic resonance imaging (MRI) is a method for obtaining an image of a tissue or structure or the like in the living body using nuclear magnetic resonance in a magnetic field.

The signal strength of magnetic resonance (MR) depends on the longitudinal relaxation time (T1), transverse relaxation time (T2) and the like. Consequently, the contrast of the resulting image may be increased by controlling T1 or T2.

For example, since a gadolinium ion ($Gd^{3+}$) exhibits paramagnetic properties and reduces T1 and T2, it is expected to have a significant effect as an MRI contrast agent. However, a free gadolinium ion has biological toxicity. Accordingly, a complex (hereinafter referred to as a "gadolinium complex"), which is stabilized by coordinating an organic ligand to a gadolinium ion, has been used as a contrast agent, and many proposals have been made regarding it (refer to U.S. Pat. No. 5,695,739, U.S. Pat. No. 5,798,092, U.S. Pat. No. 6,039,931, U.S. Pat. No. 6,149,890 and U.S. Pat. No. 6,177,562).

The T1-reducing effect of $Gd^{3+}$ is considered to depend on the coordination of a free water molecule to $Gd^{3+}$. On the other hand, a gadolinium complex, which is generally used as an MRI contrast agent, forms a chelate complex by the coordination of 7 or 8 coordinating functional groups (N or COOH) in a ligand to $Gd^{3+}$. If $Gd^{3+}$ is a metal ion in a nine-coordination geometry, it is more likely that the T1-reducing ability intrinsic to $Gd^{3+}$ is not sufficiently derived from such a general gadolinium complex. This point is the same as in the case of a complex using a metal ion other than $Gd^{3+}$.

DISCLOSURE OF THE INVENTION

Accordingly, an object of the present invention is to provide a metal complex that exhibits a T1-reducing effect superior to that of a conventional one, a compound which is a ligand used for the metal complex and an intermediate compound used for the production of the metal complex. In addition, another object of the present invention is to provide an MRI contrast agent which exhibits a T1-reducing effect superior to that of a conventional MRI contrast agent.

A compound with a cyclic structure according to the present invention is characterized by being a compound represented by the following Formula (A):

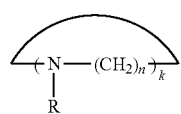

(A)

[in Formula (A), n is an integer of 1 or more, k is an integer of 3 or more and 8 or less, R represents a group represented by the following Formula (1):

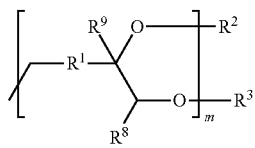

(1)

(in Formula (1), $R^1$ is an arylene group which may have a substituent, an alkylene group which may have a substituent or a group in which an arylene group which may have a substituent and an alkylene group which may have a substituent are bonded together, $R^8$ is H, an alkyl group, a halogenated alkyl group, an alkoxyl group, an aryl group, an aryloxy group, a silyl group, a silyloxy group or $COOR^{10}$ ($R^{10}$ is H, an aryl group or an alkyl group), $R^9$ is H, an alkyl group, a halogenated alkyl group, an alkoxyl group, an aryl group, an aryloxy group, a silyl group, a silyloxy group or $COOR^{10}$ ($R^{10}$ is H, an aryl group or an alkyl group), m is an integer of 1 or more, and $R^2$ and $R^3$ are an end-group represented by the following Formula (2-1):

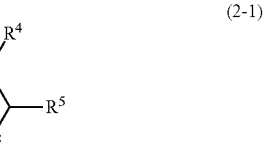

(2-1)

(in Formula (2-1), $R^1$ is an arylene group which may have a substituent, an alkylene group which may have a substituent or a group in which an arylene group which may have a substituent and an alkylene group which may have a substituent are bonded together, $R^8$ is H, an alkyl group, a halogenated alkyl group, an alkoxyl group, an aryl group, an aryloxy group, a silyl group, a silyloxy group or $COOR^{10}$ ($R^{10}$ is H, an aryl group or an alkyl group), $R^9$ is H, an alkyl group, a halogenated alkyl group, an alkoxyl group, an aryl group, an aryloxy group, a silyl group, a silyloxy group or $COOR^{10}$ ($R^{10}$ is H, an aryl group or an alkyl group), and $R^4$ and $R^5$ are each independently H, OH, COOH, $NH_2$, an alkyl group which may have a substituent or an alkoxyl group which may have a substituent), or an end-group with a five-ring structure represented by the following Formula (2-2):

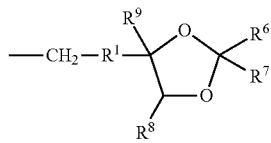

(2-2)

(in the Formula (2-2), $R^1$ is an arylene group which may have a substituent, an alkylene group which may have a substituent or a group in which an arylene group which may have a substituent and an alkylene group which may have a substituent are bonded together, $R^8$ is H, an alkyl group, a halogenated alkyl group, an alkoxyl group, an aryl group, an aryloxy group, a silyl group, a silyloxy group or $COOR^{10}$ ($R^{10}$ is H, an aryl group or an alkyl group), $R^9$ is H, an alkyl group, a halogenated alkyl group, an alkoxyl group, an aryl group, an aryloxy group, a silyl group, a silyloxy group or $COOR^{10}$ ($R^{10}$ is H, an aryl group or an alkyl group), and $R^6$ and $R^7$ are each independently H, an alkyl group which may have a substituent or an alkoxyl group which may have a substituent), when m is an integer of 2 or more, to at least one of the $R^2$ side and $R^3$ side of a first repeating unit containing $R^1$, the methylene group side of a next repeating unit containing $R^1$ is bonded, and this bonding is repeated according to the value of m)], provided that a compound in which all $R^4$ and $R^5$ in the group represented by Formula (2-1) are COOH is excluded.

A metal complex of the present invention is characterized in that the compound in the above Formula (A) is bonded to a metal ion with a T1-reducing effect by a coordination bond. A contrast agent of the present invention is characterized by containing the metal complex as a contrast component.

A compound, which is useful as a raw material compound for the synthesis of a compound of the above Formula (A) according to the present invention, is characterized by being represented by the following Formula (3):

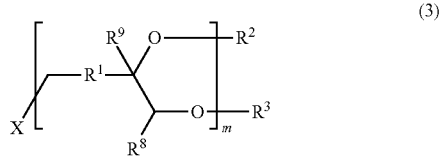

(3)

(in Formula (3), X is halogen, $R^1$ is any of an arylene group which may have a substituent, an alkylene group which may have a substituent or a group in which an arylene group which may have a substituent and an alkylene group which may have a substituent are bonded together, $R^8$ is H, an alkyl group, a halogenated alkyl group, an alkoxyl group, an aryl group, an aryloxy group, a silyl group, a silyloxy group or $COOR^{10}$ ($R^{10}$ is H, an aryl group or an alkyl group), $R^9$ is H, an alkyl group, a halogenated alkyl group, an alkoxyl group, an aryl group, an aryloxy group, a silyl group, a silyloxy group or $COOR^{10}$ ($R^{10}$ is H, an aryl group or an alkyl group), m is an integer of 1 or more, and $R^2$ and $R^3$ are an end-group represented by the following Formula (2-1):

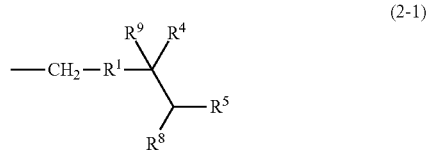

(2-1)

(in Formula (2-1), $R^1$ is any an arylene group which may have a substituent, an alkylene group which may have a substituent or a group in which an arylene group which may have a substituent and an alkylene group which may have a substituent are bonded together, $R^8$ is H, an alkyl group, a halogenated alkyl group, an alkoxyl group, an aryl group, an aryloxy group, a silyl group, a silyloxy group or $COOR^{10}$ ($R^{10}$ is H, an aryl group or an alkyl group), $R^9$ is H, an alkyl group, a halogenated alkyl group, an alkoxyl group, an aryl group, an aryloxy group, a silyl group, a silyloxy group or $COOR^{10}$ ($R^{10}$ is an aryl group or an alkyl group), and $R^4$ and $R^5$ are each independently H, OH, COOH, $NH_2$, an alkyl group which may have a substituent or an alkoxyl group which may have a substituent), or an end-group having a five-ring structure represented by the following Formula (2-2):

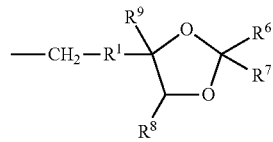

(2-2)

(in the Formula (2-2), $R^1$ is an arylene group which may have a substituent, an alkylene group which may have a substituent or a group in which an arylene group which may have a substituent and an alkylene group which may have a substituent are bonded together, $R^8$ is H, an alkyl group, a halogenated alkyl group, an alkoxyl group, an aryl group, an aryloxy group, a silyl group, a silyloxy group or $COOR^{10}$ ($R^{10}$ is H, an aryl group or an alkyl group), $R^9$ is H, an alkyl group, a halogenated alkyl group, an alkoxyl group, an aryl group, an aryloxy group, a silyl group, a silyloxy group or $COOR^{10}$ ($R^{10}$ is H, an aryl group or an alkyl group), and $R^6$ and $R^7$ are each independently H, an alkyl group which may have a substituent or an alkoxyl group which may have a substituent), when m is an integer of 2 or more, to at least one of the $R^2$ side and $R^3$ side of a first repeating unit containing $R^1$, the methylene group side of a next repeating unit containing $R^1$ is bonded, and this bonding is repeated according to the value of m).

A method for producing a compound of the above Formula (A) according to the present invention is characterized by comprising at least a step of reacting a cyclic structure compound represented by the following Formula (B) and a compound represented by the above Formula (3):

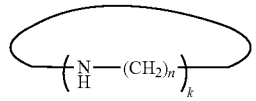

(B)

(in Formula (B), n is an integer of 1 or more and k is an integer of 3 to 8.)

A method for producing a metal complex according to the present invention is characterized by comprising at least a step of coordinating the compound represented by the above Formula (A) to a metal ion with a T1-reducing effect.

Further features of the present invention will become apparent from the following description of exemplary embodiments (with reference to the attached drawings).

BRIEF DESCRIPTION OF THE DRAWINGS

FIG. 9A shows an image before the administration of a complex, and FIG. 9B shows an image after the administration of a Gd triamine 2nd G-12-ol-dendrimer complex (11).

BEST MODES FOR CARRYING OUT THE INVENTION

Figure 1:
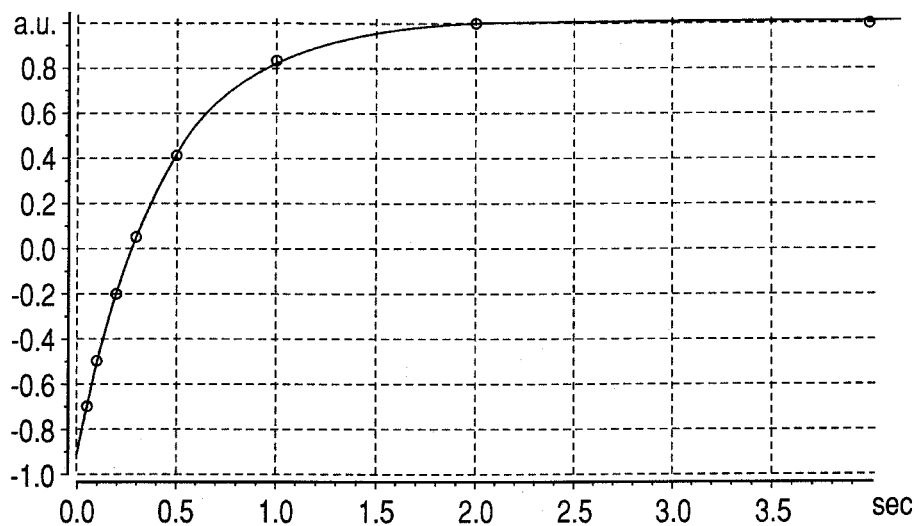
FIG. 1 shows T1 relaxation time measurement data of a sample water prepared by adding 10% heavy water to an aqueous solution of 0.13 mM complex (R)-11, as measured by using a 500 MHz NMR apparatus in Example 4.

A compound with a cyclic structure according to the present invention is represented by the following Formula (A):

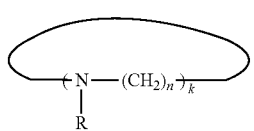

(A)

a unit comprising —N—(CH$_2$)$_n$— is serially repeated in predetermined numbers and both ends are bonded to form a structure comprising a ring chain. A core site is formed by the cyclic structure, and multiple Ns in the ring chain of the core site form a coordination site of a metal ion.

n in the Formula (A) is an integer of 1 or more and k is an integer from 3 to 8. Further, the value of n may be different for each —N—(CH$_2$)$_n$—.

R in Formula (A) is a side chain to the core site and has a structure with the following Formula (1):

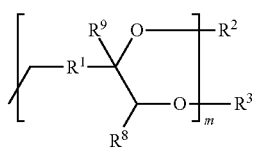

(1)

(in the Formula (1), R$^1$ is an arylene group which may have a substituent, an alkylene group which may have a substituent or a group in which an arylene group which may have a substituent and an alkylene group which may have a substituent are bonded together, R$^8$ is H, an alkyl group, a halogenated alkyl group, an alkoxyl group, an aryl group, an aryloxy group, a silyl group, a silyloxy group or COOR$^{10}$ (R$^{10}$ is H, an aryl group or an alkyl group), R$^9$ is H, an alkyl group, a halogenated alkyl group, an alkoxyl group, an aryl group, an aryloxy group, a silyl group, a silyloxy group or COOR$^{10}$ (R$^{10}$ is H, an aryl group or an alkyl group), m is an integer of 1 or more, and R$^2$ and R$^3$ are an end-group represented by the following Formula (2-1):

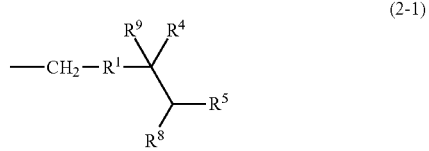

(2-1)

(in Formula (2-1), R$^1$ is an arylene group which may have a substituent, an alkylene group which may have a substituent or a group in which an arylene group which may have a substituent and an alkylene group which may have a substituent are bonded together, R$^8$ is H, an alkyl group, a halogenated alkyl group, an alkoxyl group, an aryl group, an aryloxy group, a silyl group, a silyloxy group or COOR$^{10}$ (R$^{10}$ is H, an aryl group or an alkyl group), R$^9$ is H, an alkyl group, a halogenated alkyl group, an alkoxyl group, an aryl group, an aryloxy group, a silyl group, a silyloxy group or COOR$^{10}$ (R$^{10}$ is H, an aryl group or an alkyl group), and R$^4$ and R$^5$ are each independently H, OH, COOH, NH$_2$, an alkyl group which may have a substituent or an alkoxyl group which may have a substituent), or an end-group with a five-ring structure represented by the following Formula (2-2):

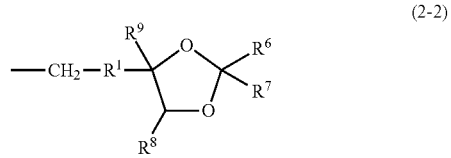

(2-2)

(in the Formula (2-2), R$^1$ is an arylene group which may have a substituent, an alkylene group which may have a substituent or a group in which an arylene group which may have a substituent and an alkylene group which may have a substituent are bonded together, R$^8$ is H, an alkyl group, a halogenated alkyl group, an alkoxyl group, an aryl group, an aryloxy group, a silyl group, a silyloxy group or COOR$^{10}$ (R$^{10}$ is H, an aryl group or an alkyl group), R$^9$ is H, an alkyl group, a halogenated alkyl group, an alkoxyl group, an aryl group, an aryloxy group, a silyl group, a silyloxy group or COOR$^{10}$ (R$^{10}$ is H, an aryl group or an alkyl group), and R$^6$ and R$^7$ are each independently H, an alkyl group which may have a substituent or an alkoxyl group which may have a substituent).

In each formula, as the substituent on R$^1$, that increases the water-solubility of the finally obtained metal complex is preferred. On the other hand, the substituent on R$^1$ is preferably a group that is not coordinated to a central metal during the formation of a metal complex. In view of the above considerations, the substituent on R$^1$ is preferably an ether group.

Specific preferable examples of $R^1$ include an arylene group such as a phenylene group, a naphthalenediyl group, an anthracenediyl group and the like, and an arylene group with an ether group as a substituent such as an oxyphenylene group and the like; an alkyl group such as a methylene group, an ethylene group, a propylene group, a butylene group and the like; an alkyl group with an ether group as a substituent such as an oxymethylene group, an oxyethylene group, an oxypropylene group, an oxybutylene group and the like; and a group in which an arylene group which may have a substituent and an alkylene group which may have a substituent are bonded, such as a methylenephenylene group, an oxymethylenephenylene group, an oxyphenylenemethylene group and the like.

Further, when m is 1 or more, the preferred range is 1 or more and 8 or less.

When $R^4$ or $R^5$ is an alkyl group or an alkoxy group, the preferred carbon number is 1 or more and 3 or less. In addition, when $R^6$ or $R^7$ is an alkyl group, the preferred carbon number is 1 or more and 3 or less. The substituents which $R^4$, $R^5$, $R^6$ and $R^7$ may have include halogen, $NH_3$, COOH and the like.

When $R^8$ is an alkyl group, a halogenated alkyl group and or alkoxyl group, the preferred carbon number is 1 or more and 3 or less. In addition, when $R^8$ is either an aryl group or an aryloxy group, the aryl portion is preferably a phenyl group. Further, when $R^8$ is either a silyl group or a silyloxy group, the silyl portion is preferably either a trimethylsilyl group or a trimethoxysilyl group. When $R^{10}$ is either an aryl group or an alkyl group, the carbon number is preferably 1 or more and 3 or less. These points are the same as in the case of $R^9$.

Hereinafter, if there is a mention of the case where both $R^8$ and $R^9$ are H for simplicity, the inside of [ ] in Formula (1) represents a repeating unit shown in the following Formula (4).

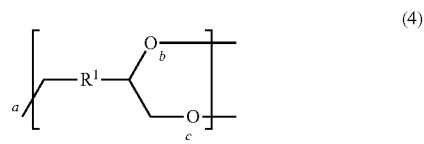

(4)

When the structure is repeated, to at least one of the O side ($R^2$ side and $R^3$ side) a first repeating unit containing $R^1$, the methylene group side of a next repeating unit containing $R^1$ is bonded, and the bonding is repeated according to the value of m. When it is described using the formula of the repeating unit, the next repeating unit is bonded to at least one of position b of the $R^2$ side and position c of the $R^3$ side at position a of the methylene group side. Further, the repeating unit is bonded depending on the value of m and elongation of the side chain is ultimately stopped in a state where $R^2$ and $R^3$ are bonded to the ends. When the next repeating unit is constantly bonded to position b and position c at position a, a branched chain is obtained in which every time the repeating unit is added, the number of the repeating units is increased by the square of the addition number. Thus, the total number of the repeating units is $\Sigma m^2$. A structure in the case of m=2 to 4 is described below.

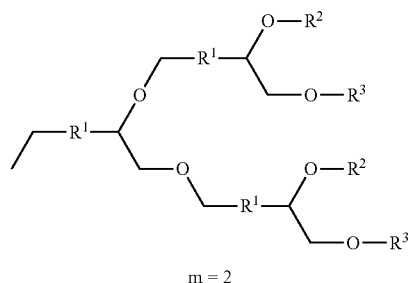

m = 2

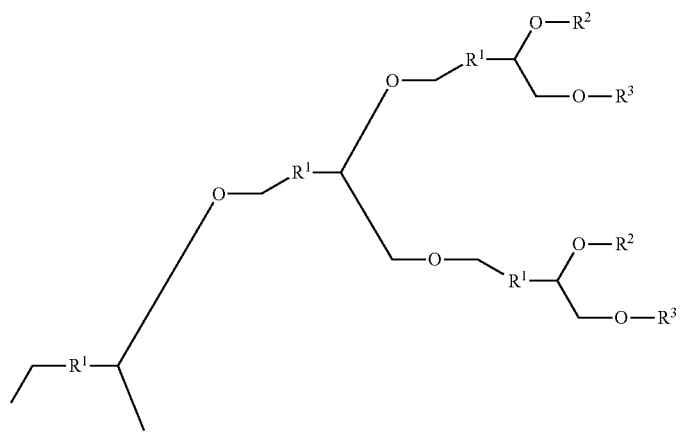

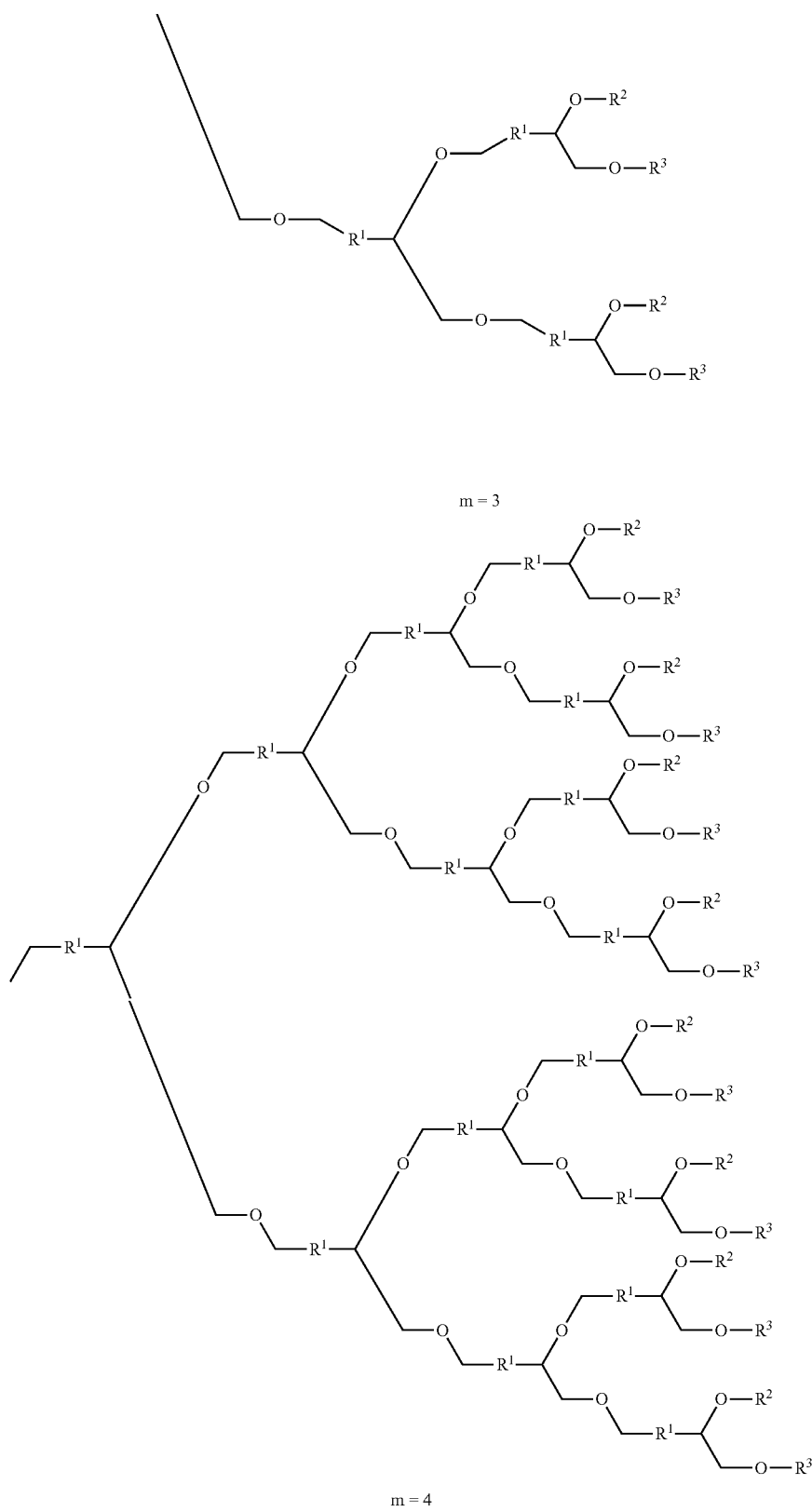
As such a branched structure, one in which $R^1$ is the same between each repeating unit, the repeating unit is bonded to both b and c shown above and the repeating unit is increased by the square of the number of the repeating units is preferred.

R¹ is an arylene group which may have a substituent, an alkylene group which may have a substituent or a group in which an arylene group which may have a substituent and an alkylene group which may have a substituent are bonded, and is independent for each repeating unit when there are several of the above repeating units. Thus, R¹ may be different in each repeating unit. In addition, an end-group with R² and R³ represents an end-group that is independent of each end-group and is represented by the above-described Formula (2-1) or Formula (2-2). Of these, a group in which R¹ in each repeating unit is the same and each end-group is the same is preferred.

In the case of m=2, as a specific example when R² and R³ are linked to form a five-ring structure together with a structure containing two oxygen atoms in the repeating unit, there may be a compound (R)-9 in Examples described later.

A specific example of the portion shown by Formula (1) of the compound represented by Formula (A) is shown below.

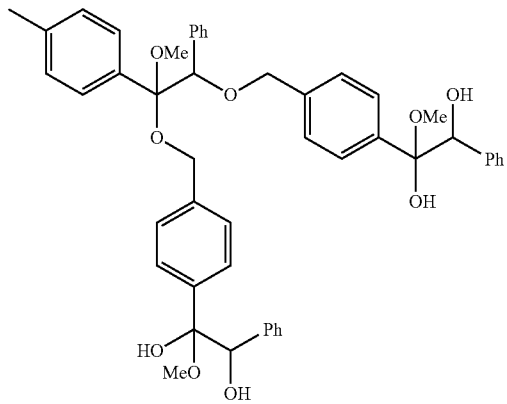

(1-3)

(In Formula (1-3), Me represents a methyl group and Ph represents a phenyl group.)

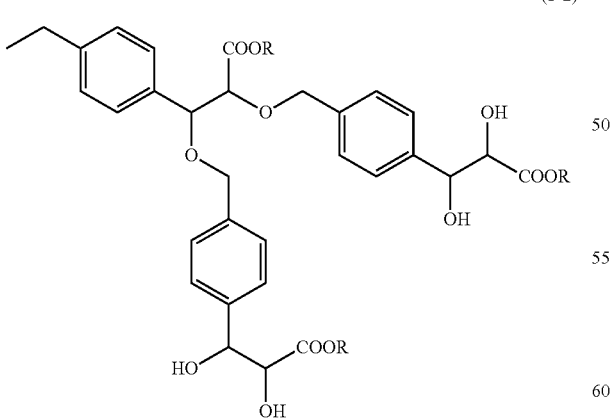

(1-1)

(1-2)

(In Formula (1-2), Rs each independently represent H, an alkyl group or an aryl group.)

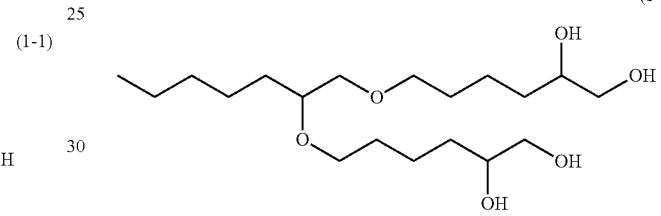

(1-4)

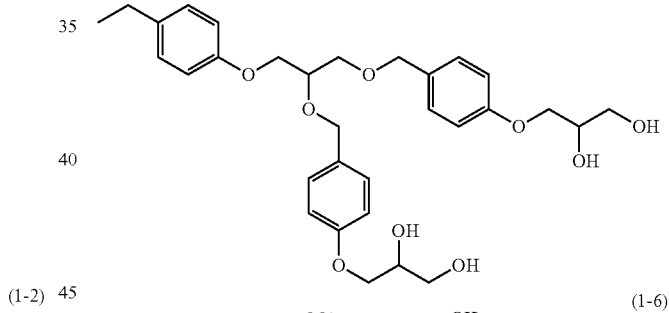

(1-5)

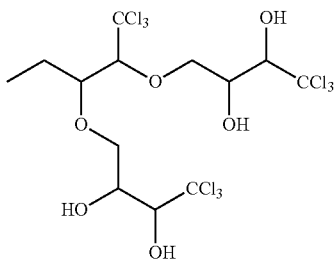

(1-6)

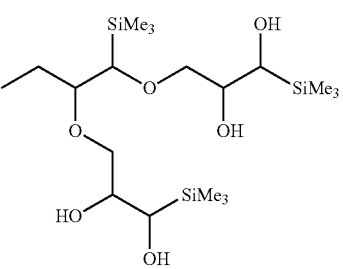

(1-7)

(In Formula (1-7), Me represents a methyl group.)

Of these, in view of the solubility when used for preparing an MRI contrast agent described later, a group represented by Formula (1-1), Formula (1-2), Formula (1-4) or Formula (1-5) is preferred.

Further, among the compounds of the Formula (A), those in which all $R^4$ and $R^5$ in the group represented by Formula (2-1) are COOH are excluded from the scope of the present invention.

The coordination site of the compound in Formula (A) may be coordinated to a metal ion with a T1-reducing effect to obtain a metal complex that is useful as a contrast component (effective component) of a contrast agent. Here, the metal ion with a T1-reducing effect includes any of a lanthanoid ion, a manganese ion, a chromium ion, an iron ion and the like. Further, an MRI contrast agent may be prepared by using at least one of these metal complexes as an effective component.

As the raw material for producing the compound in Formula (A), a compound represented by the following Formula (3) is preferred.

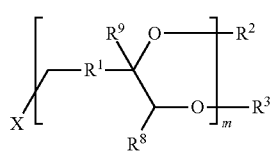

(3)

In Formula (3), X is a halogen atom and m, $R^1$ to $R^3$, $R^8$ and $R^9$ are defined in the same manner as in Formula (1).

The compound represented by the Formula (A) may be produced by a method comprising at least one step of reacting a cyclic structure compound represented by the following Formula (B) with a compound represented by Formula (3).

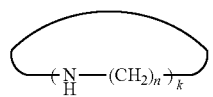

(B)

(In Formula (B), n is an integer of 1 or more and k is an integer of 3 to 8.) Further, a metal complex may be produced according to the present invention by a method that includes at least one step of coordinating the compound of the Formula (A) to a metal ion having the T1-reducing effect. In these production methods, an asymmetric dihydroxylation is preferably used for the synthesis of a compound in Formula (3). In addition, there may be added a step of hydrolyzing a five-ring structure after a compound in which the end-group has a five-ring structure which is used as the compound in Formula (3) is reacted with a cyclic structure compound represented by Formula (B).

Among the compounds represented by Formula (B), a commercially available one may be used as a compound in which k is 3 or more and 6 or less. A compound in which k is 7 or 8 may be synthesized by a well-known synthetic method (For the former, for example, Atkins, T. J.; Richman, J. E.; Dettle, W. F. Org. Synth. 1978, 58, 86. For the latter, for example, Bianchi, A.; Mangani, S.; Micheloni, M.; Nanini, V.; Orioli, P.; Paoletti, P.; Seghi, B. Inorg. Chem. 1985, 24, 1182). In addition, a compound in which n is different for each (—NH(CH$_2$)$_n$—) may be obtained by purchasing a commercially available product or through synthesis. For example, a cycloamine that includes (—NH(CH$_2$)$_2$—) and (—NH(CH$_2$)$_3$—) in which k is 4 is available commercially.

In view of the coordination ability, in a compound represented by Formula (A) and a compound represented by Formula (B), the value (that is, the number of atoms constituting a ring) represented by k(n+1) is preferably 8 or more and 24 or less.

(First Compound: Ligand)

A compound represented by the Formula (A) according to the present invention is a compound that can become a ligand of a chelate complex. The specifically preferred embodiment of the compound includes, for example, a compound of the following Formula (5).

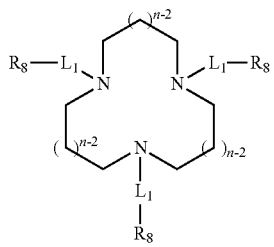

(5)

Where $L_1$ is a portion of the side chain represented by the above Formula (1), $R_8$ comprehensively represents the end of the side chain and corresponds to $R^2$ and $R^3$ in Formula (2) (which is abbreviated for simplicity and multiple ends are present in each $L_1$).

Here, the important point is in that at least one of the end-most ends (hereinafter simply referred to as an "end") of the end portions is other than COOH. When a complex is formed, it is considered that COOH is strongly coordinated to a central metal ion such as $Gd^{3+}$ and the like. When all of the ends are strongly coordinated to a central metal ion, since the probability that free water is coordinated is significantly reduced, the T1-reducing effect of a central metal is considered to be impaired. Further, when a structure represented by the above Formula (2-2) is selected as an end portion of the side chain, before being used as a ligand, it is preferably dihydroxylated by hydrolyzing at least part of it.

The end portion of the side chain may be arbitrarily designed depending on the kind of central metal ion or the structure of other portions of the ligand or the like. With regard to relatively difficult coordination to the central metal ion, an OH group is preferably selected as at least one of the ends. As the value of n or k of the core of a cyclic structure represented by Formula (B), a suitable value may be selected primarily depending on the kind of central metal ion. The preferred value of k is an integer of 3 or more and 5 or less. In addition, the preferred value of n is an integer of 2 or more and 4 or lees. Further, m in the Formula (1) is an integer of 1 or more and preferably 1 or more and 9 or less. From the standpoint of the ease of synthesis, these values are preferably odd numbers (the number of $R^1$ is an even number when counted together with the end portion). Representative values of m include 1 and 3. In addition, since the structure of Formula (1) contains an asymmetric carbon atom, the first compound may be an optically active compound. This is the same as in the case of the following compounds.

(Second Compound: Metal Complex)

A second compound of the present invention is a metal complex with a structure in which the above first compound is coordinated to a metal ion. As the central metal ion, an ion with a T1-reducing effect is selected. Such a metal ion can include lanthanoid ion, manganese ion, chromium ion and iron ion, and gadolinium ion is preferable.

The second compound of the present invention has an excellent T1-reducing effect because many free water molecules can get close to the central metal ion compared to the conventional complex for an MRI contrast agent.

In addition, the T1-reducing effect may be increased by reducing the mobility of the molecules of a complex themselves. Such reduction of the mobility of the molecules themselves may be achieved by increasing the molecular weight of the molecules of a complex, especially a ligand. Since the second compound of the present invention has a considerably large molecular weight compared to a complex for a commercially available MRI contrast agent, the T1-reducing effect is further increased due to the reduction of the mobility of the molecules of a complex themselves.

Further, when the second complex is used as an MRI contrast agent, the stability of the complex itself is one of the important performance factors. The second compound of the present invention contributes to the stability of the complex itself by a protecting effect due to the high cubic bulk of the ligand.

Furthermore, the present invention is an excellent method for synthesizing a ligand with such a large molecular weight both uniformly and selectively.

(Third Compound: Intermediate Compound to be a Side Chain of a Ligand)

A third compound of the present invention is a compound represented by the Formula (3) described previously. This compound can be used as an intermediate for the synthesis of the compound in Formula (1).

(For Synthesizing a Ligand)

For synthesizing a ligand, it is preferable that a side chain represented by the Formula (3) be synthesized and then reacted with a compound represented by the Formula (B) to form the core of a cyclic structure. For synthesizing the side chain, an asymmetric dihydroxylation is preferred. The specific technique is described later in the Examples. In addition, regarding the process for synthesizing a side chain using asymmetric dihydroxylation, a report by the present inventors, Kondo et al. "H.-T. Chang, C.-T. Chen, T. Kondo, G. Siuzdak, and K. B. Sharpless, Asymmetric Dihydroxylation Enables Rapid Construction of Chiral Dendrimers, Agnew. Chem., 35, 182 (1996)", is used as a reference. In addition, only a single diastereomer may be synthesized by using asymmetric dihydroxylation.

(MRI Contrast Agent)

An MRI contrast agent of the present invention contains the above-mentioned metal complex (second compound of the present invention). The second compound of the present invention may be used alone as an MRI contrast agent and may be mixed with other compounds and the like which can function as a contrast component for use as an MRI contrast agent. In addition, the second compound may be used by mixing it with a carrier or diluent where necessary. As mentioned above, since the second compound of the present invention has an excellent T1-reducing effect, it is suitable as an MRI contrast agent.

To increase clearance in the kidney, the second compound should preferably have a structure with increased water-solubility (specifically, a water-soluble group such as an ether group, a COOH group and the like should be introduced as mentioned above). On the other hand, if the second compound has a structure in which the water-solubility is not too increased and the lipid-solubility is increased to some extent, the retention properties in the liver can be improved and the contrast effect in the liver can be increased.

EXAMPLES

Example 1

An intermediate was synthesized according to the following scheme.

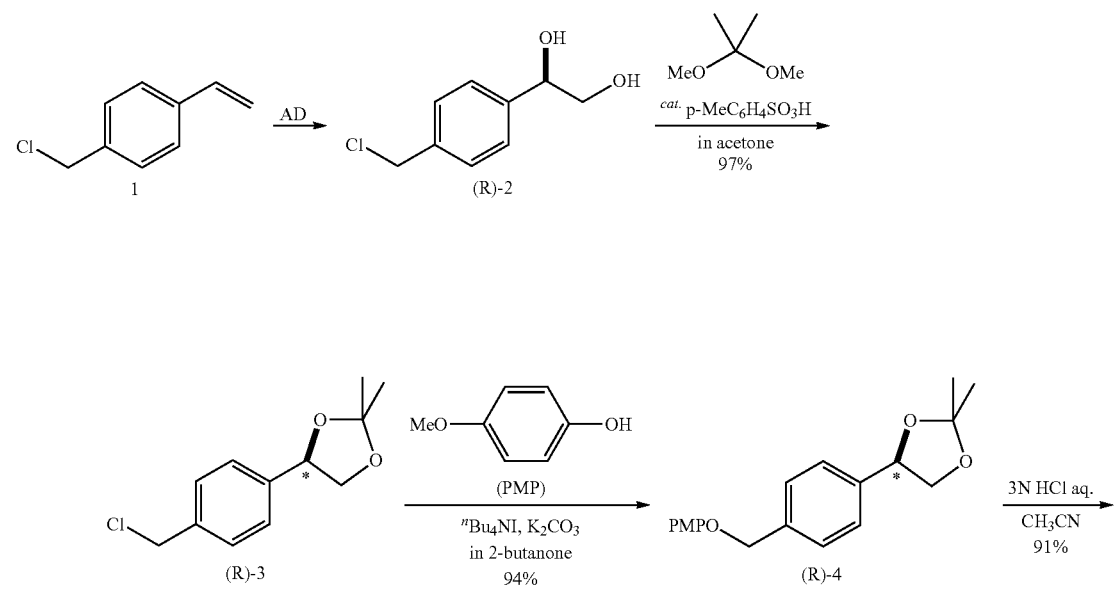

-continued

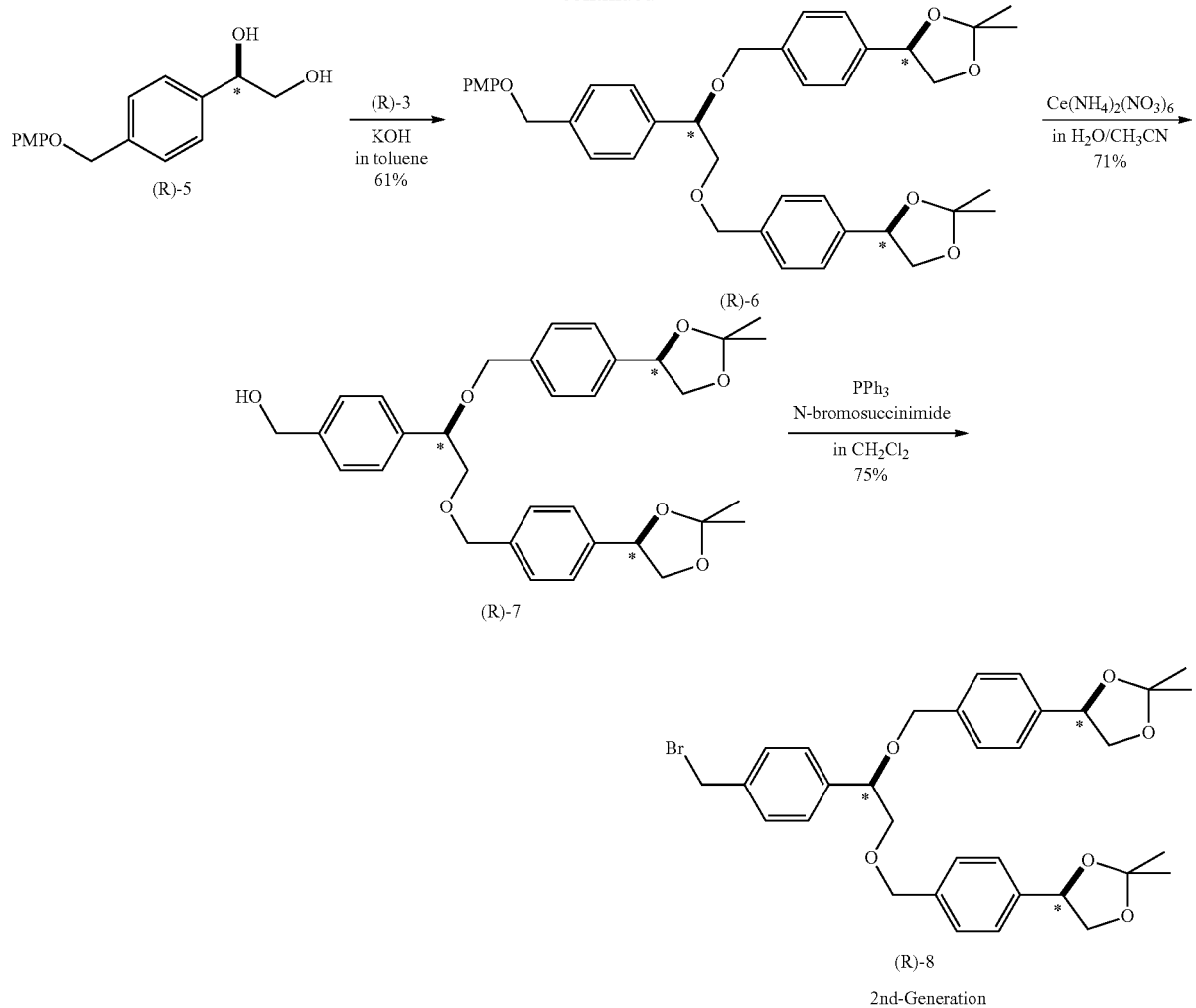

1. Synthesis of (R)-2

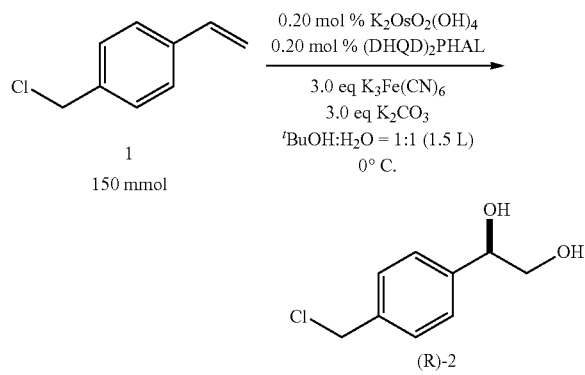

To a 2 L reactor were added 114 mg of $K_2OsO_2(OH)_4$ catalyst, 234 mg of $(DHQD)_2PHAL$ ligand, 148 g of $K_3Fe(CN)_6$ and 61.8 g of $K_2CO_3$, and these were mixed well by shaking. Subsequently, to the reactor was added a mixed solution of ice water and $^tBuOH$ with a volume ratio of 1:1. The reaction mixture was cooled in a cooling bath to 0° C., 22.8 g of a substrate 1 was added and the mixture was stirred at 0° C. under air for 4 hours.

After the reaction was complete, the reaction mixture was returned to room temperature by removing the cooling bath, 225 g of sodium sulfite ($Na_2SO_3$) was added, and the mixture was stirred for one hour or less. After stirring was complete, the yellow organic layer was concentrated by an evaporator. The water layer was extracted with ethyl acetate. To the residue obtained after the evaporator was added the extracted solution, and the mixture was concentrated once again by the evaporator. Thereafter, the residue was recrystallized from a mixed solvent of hexane and ethyl acetate. After recrystallization, the resulting product was filtered off to obtain a colorless needle crystal. The filtrate was concentrated once again, and then subjected to recrystallization. The resulting crystals were all collected and recrystallized several times to obtain a product (R)-2.

The resulting product was checked by HPLC equipped with a chiral column. The various conditions of the HPLC analysis were as follows.

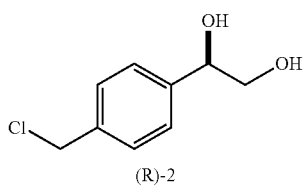

(R)-2

RT = c.a. 11~14 min
Column: CHIRALCEL OJ
Eluent: Hexane/2-propanol (9/1)
Flow rate: 1.0 ml/min
Detection: UV254 nm
Temp: 40° C.

2. Synthesis of (R)-3

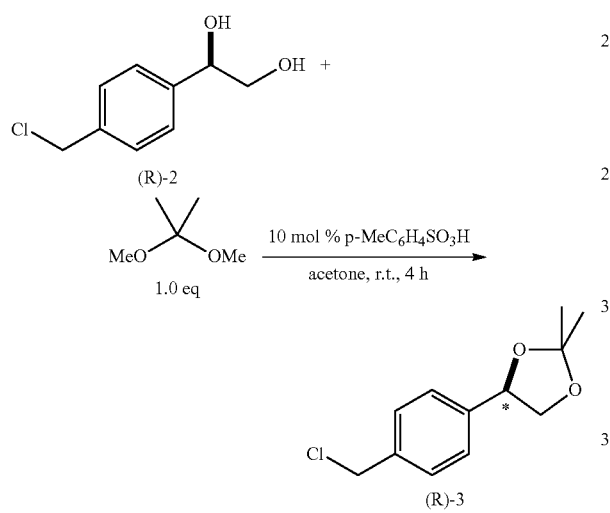

To a reactor were added (R)-2, acetone, 2,2-dimethoxypropane and p-toluene sulfonic acid in this order, and the mixture was stirred at room temperature under air for 4 hours. After the reaction was complete, to the reaction mixture was added a 10% NaOH aqueous solution. During this stage, an orange-colored insoluble product (by-product) was precipitated. The precipitated product was directly concentrated by an evaporator and the residue was extracted with ethyl acetate. The organic layer was dehydrated with brine and magnesium sulfate, and then concentrated once again by the evaporator. The residue was isolated and purified by column chromatography (neutral alumina) (developing solvent: ethyl acetate:hexane=1:4 to 1:1) to obtain (R)-3 as a slightly yellowish colorless liquid.

3. Synthesis of (R)-4

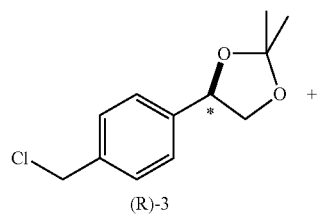

(R)-3

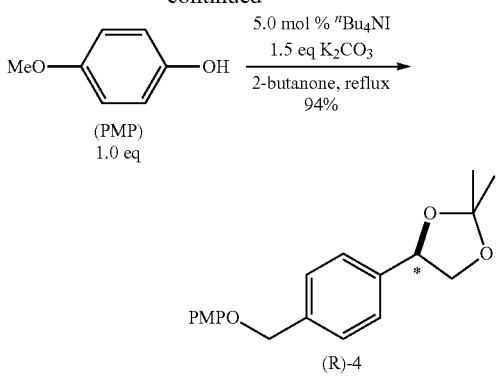

To a reactor were added (R)-3, p-methoxyphenol, tetra-n-butylammonium iodide and potassium carbonate, and the reaction mixture was heated under reflux in 2-butanone under air for 48 hours. After the reaction was complete, the unreacted potassium carbonate was removed by filtration and the filtrate was concentrated by an evaporator. The residue was transferred to a separating funnel and extracted by adding water and ethyl acetate. The organic layer was dehydrated with magnesium sulfate and brine, and then concentrated by the evaporator. The resulting crude product was purified by column chromatography (neutral alumina, developing solvent: ethyl acetate:hexane=1:1 to 100:0) to obtain a colorless solid (R)-4. In the structural Formula (R)-4, PMP is a 4-methoxyphenyl group. In addition, purification may be performed by recrystallization (hexane and ethyl acetate).

4. Synthesis of (R)-5

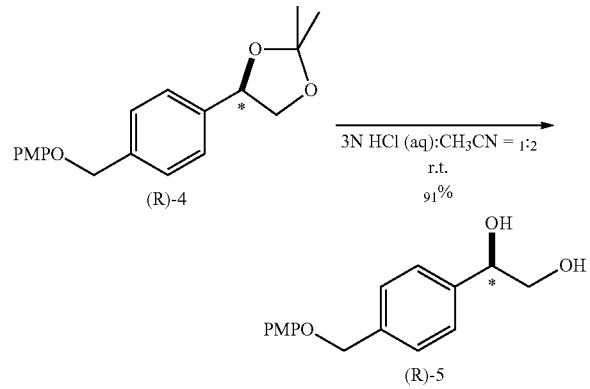

To a reactor were added (R)-4 and acetonitrile, and the mixture was stirred under air. To the uniform solution was added 3N hydrochloric acid. After a while, a product began to precipitate as a white solid. After two or three hours had passed, the precipitated product was concentrated by an evaporator and the residue was filtered to obtain a product that was a while solid. The filtered product was washed with acetonitrile to remove the residual moisture. The filtrate was concentrated once again by the evaporator, filtered and washed with acetonitrile. The crude product collected was purified by recrystallization (ethyl acetate) to obtain a colorless solid (R)-5.

5. Synthesis of (R)-6

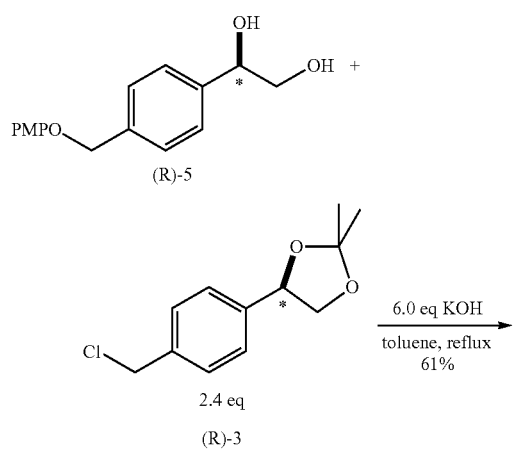

Into a reaction apparatus equipped with a Dean-Stark tube and a reflux cooling tube was placed (R)-5, and the inside of the system was replaced with argon. Subsequently, (R)-3 and toluene were added to the reactor under a flow of argon. The mixture was heated and stirred for approximately 30 minutes to make a uniform solution. To the resulting uniform solution was added KOH to make an orange-colored, cloudy solution. Thereafter, the solution was heated under reflux for 12 hours. After the reaction was complete, the resulting solution was concentrated by an evaporator. After the concentration, a highly viscous, orange-colored crude product was obtained. The crude product was dissolved in methylene chloride. Ethyl acetate and hexane were added, and suction filtration to gave an orange-colored uniform solution. The solution was concentrated by an evaporator and then the residue was purified by column chromatography (neutral alumina) to obtain (R)-6.

6. Synthesis of (R)-7

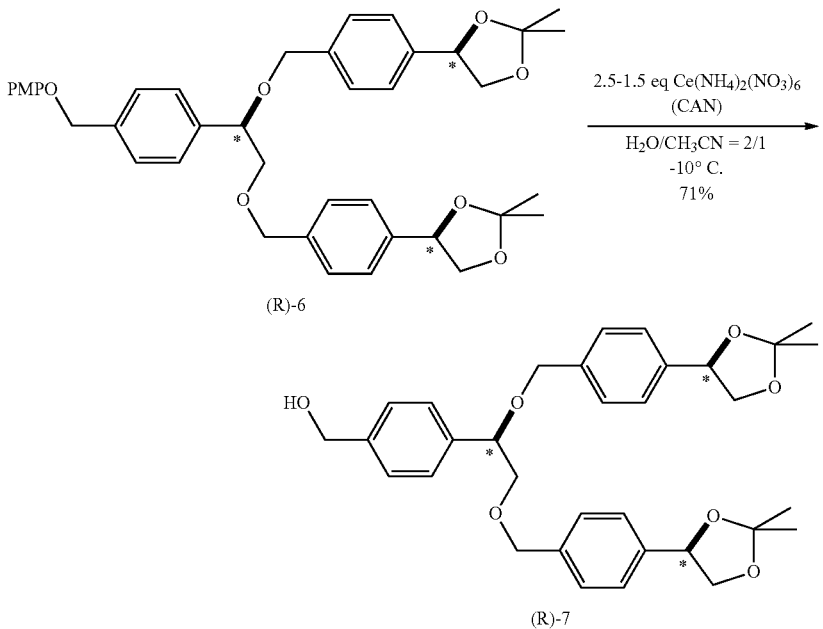

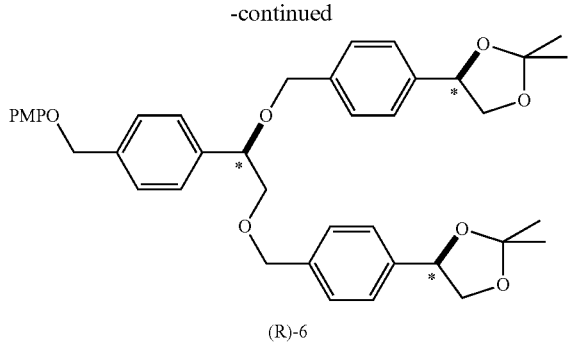

To a reactor were added (R)-6 and acetonitrile and the reactor was immersed in a cooling bath. The reactor was cooled to −10° C. and an aqueous solution of CAN was added dropwise. After the addition was complete, the resulting mixture was stirred for 30 minutes and cooling was stopped before a large amount of water was added to stop the reaction.

The resulting mixture was transferred to a separating funnel and the water layer was extracted three times with ethyl acetate. The organic layer was collected and washed twice with a 5% $K_2CO_3$ aqueous solution. The washing solution was washed twice with ethyl acetate. The organic layer was all collected and washed with a 10% $Na_2SO_4$ aqueous solution and then with a 5% $K_2CO_3$ aqueous solution, and thereafter dehydrated with brine and $MgSO_4$ and concentrated by an evaporator. The residue was purified by column chromatography (neural silica gel, developing solvent: ethyl acetate: hexane=1:1 to 100:0) to obtain (R)-7.

7. Synthesis of (R)-8

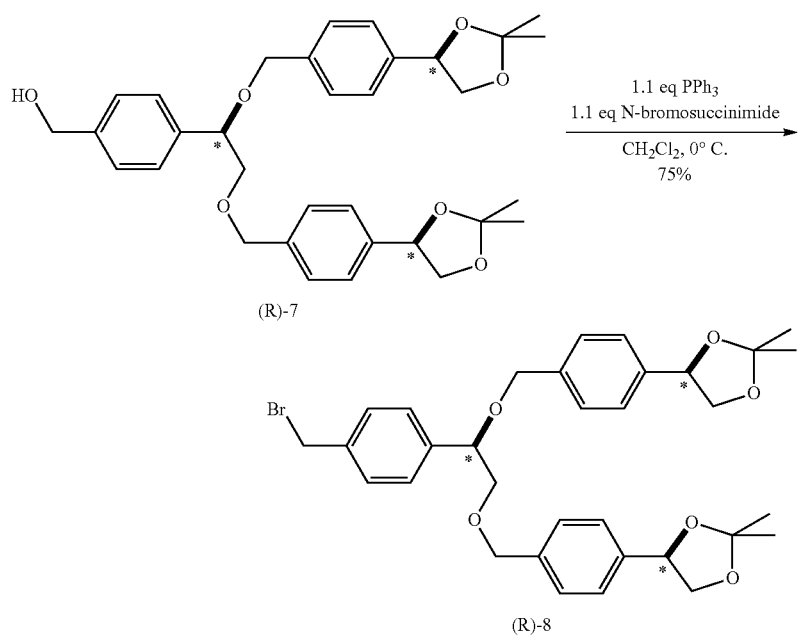

To a reactor filled with argon were added (R)-7 and methylene chloride. The reactor was immersed in a cooling bath and cooled to 0° C. PPh$_3$ and NBS were added under flowing argon. After the reaction was complete, to the reaction mixture were added diethyl ether and a saturated Na$_2$CO$_3$ aqueous solution. After the solution was separated, the organic layer was dehydrated with brine and MgSO$_4$. The resulting organic layer was concentrated by an evaporator and the residue was purified by column chromatography (neural silica gel, developing solvent: ethyl acetate:hexane=1:1) to obtain (R)-8.

Example 2

A dendrimer was synthesized according to the following scheme.

1. Synthesis of 2nd Generation-Chiral Acetonide Triamine Dendrimer (R)-9

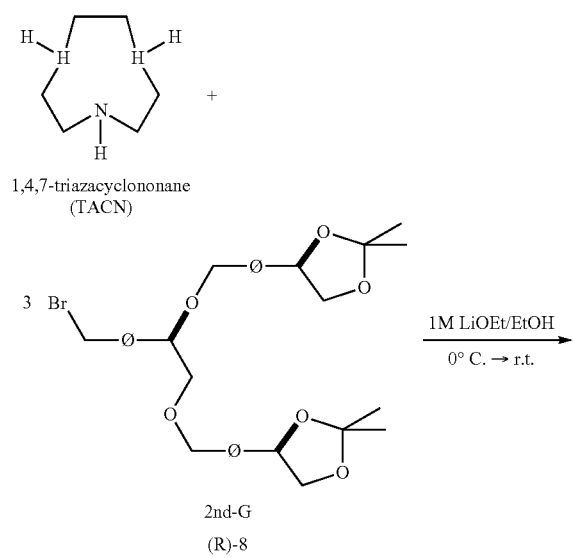

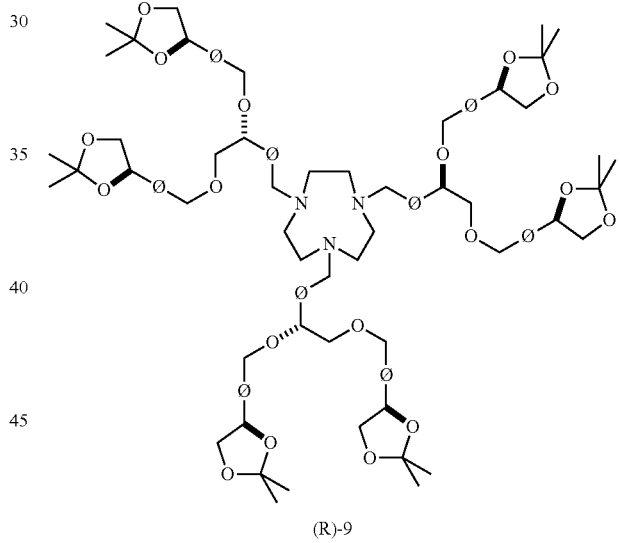

In the above scheme, "φ" represents a "phenylene group" (hereinafter the same).

To a reactor filled with argon were added TACN and (R)-8. To the reactor was added dehydrated ethanol, and the reactor was immersed in a cooling bath. After the mixture was stirred for a while, 1M LiOEt and EtOH were added and the mixture was stirred overnight while it was allowed to return to room temperature. To the resulting mixture was added brine to terminate the reaction, and extraction was performed by adding ethyl acetate. After the solution was separated, the water layer was extracted once again with ethyl acetate. The organic layer was collected and dehydrated with brine and MgSO$_4$, and then concentrated by an evaporator. The residue was purified by column chromatography (neural silica gel, developing solvent: 10% MeOH/CHCl$_3$) to obtain (R)-9 (yield: 66%).

2. Synthesis of 2nd Generation-chiral-12-ol-triamine dendrimer (R)-10

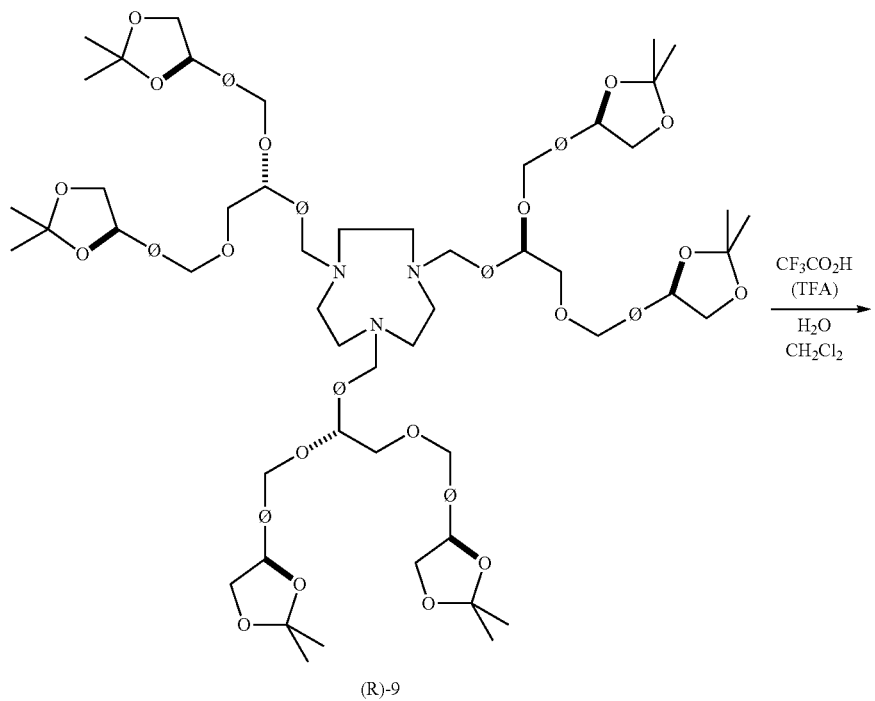

(R)-9

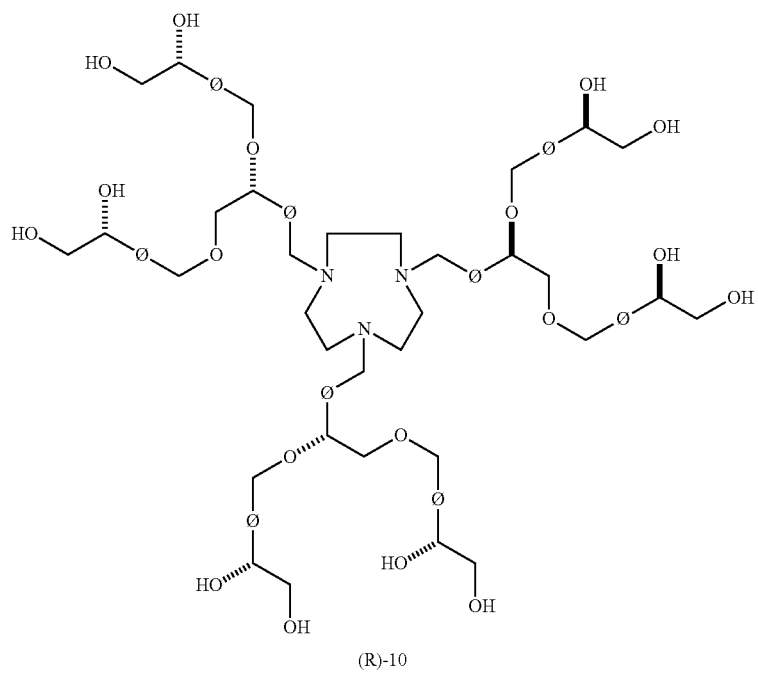

(R)-10

To a reactor were added (R)-9, water, methylene chloride and TFA in this order, and the mixture was stirred under air at room temperature. After the reaction was complete, methylene chloride and TFA were removed by drying under reduced pressure. In addition, the volume ratio of TFA to water was 4 to 1. The residue was purified by column chromatography (neural silica gel, developing solvent: 10% MeOH/CHCl$_3$) to obtain (R)-10 (yield: 80%).

Example 3

A gadolinium complex was synthesized according to the following scheme.

Synthesis of 2nd Generation-chiral-12-ol-triamine dendrimer gadolinium complex (R)-11

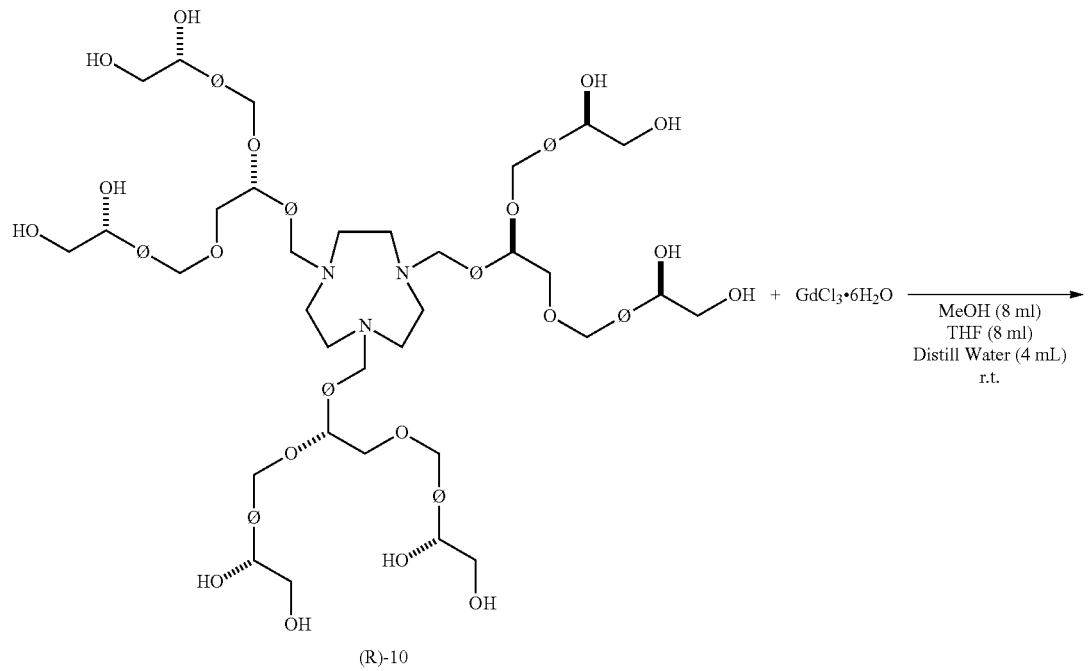

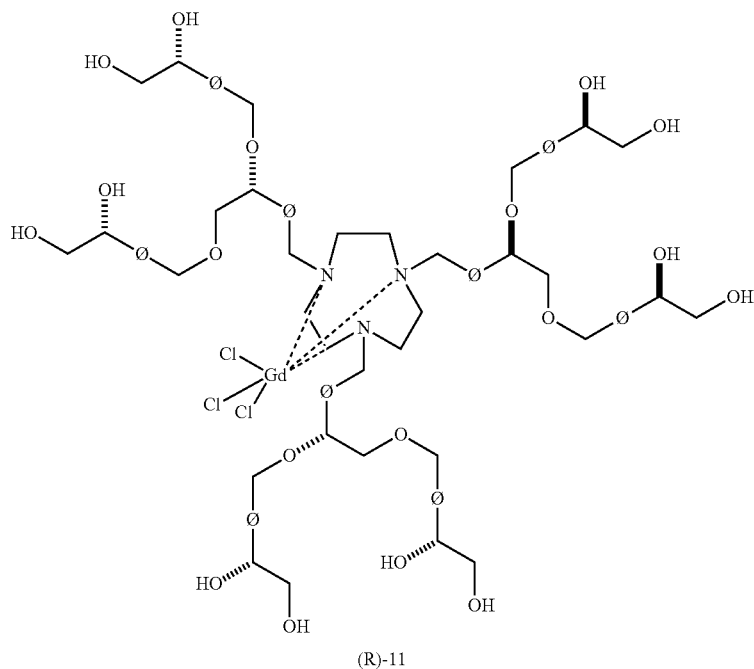

To a reactor were added (R)-10 and GdCl$_3$.6H$_2$O and to the mixture were added purified water, MeOH and THF in this order until the reaction solution became uniform. The reaction solution was stirred overnight under air at room temperature, and then freeze-dried to obtain (R)-11.

1. Compound Data 1.1: (1R)-1-[4-(chloromethyl)phenyl]ethane-1,2-diol ((R)-2) [Sample No, HTKP1-7]

Colorless solid, mp 90° C.; $^1$H NMR (CDCl$_3$, 400 MHz): 7.38 (d, J=8.3 Hz, 2H), 7.34 (d, J=8.3 Hz, 2H), 4.80 (dd, J=8.3, 3.4 Hz, 1H), 4.58 (s, 2H), 3.74 (dd, J=11.2, 3.4 Hz, 1H), 3.62 (dd, J=11.2, 8.3 Hz, 1H), 2.68 (brs, 2H); $^{13}$C NMR (CDCl$_3$, 100 MHz): 140.7, 137.2, 128.8 (2C), 126.4 (2C), 74.3, 67.9, 45.9; MS (EI) m/z 186 (M$^+$).

1.2: (4R)-4-[4-(chloromethyl)phenyl]-2,2-dimethyl-1,3-dioxolane ((R)-3) [Sample No, HTKP1-11]

Pale yellow oil, $^1$H NMR (CDCl$_3$, 400 MHz): 7.34 (s, 4H), 5.05 (dd, J=7.8, 6.3 Hz, 1H), 5.03 (dd, J=7.8, 6.3 Hz, 1H), 4.54 (s, 2H), 4.31 (dd, J=7.8, 6.3 Hz, 1H), 3.65 (t, J=7.8 Hz, 1H), 1.55 (s, 3H), 1.49 (s, 3H); $^{13}$C NMR (CDCl$_3$, 100 MHz): 139.6, 137.2, 128.8 (2C), 126.5 (2C), 109.8, 77.5, 71.6, 45.9, 26.6, 25.9; MS (EI) m/z 226 (M$^+$).

1.3: 1-[[4-((4R)-2,2-dimethyl(1,3-dioxolan-4-yl))phenyl]methoxy]-4-methoxybenzene-2,2-dimethyl-1,3-dioxolane ((R)-4) [Sample No, HTKP1-30]

Pale yellow oil, mp 93° C.; $^1$H NMR (CDCl$_3$, 400 MHz): 7.42-7.36 (m, 4H), 6.90 (d, J=9.3 Hz, 2H), 6.83 (d, J=9.3 Hz, 2H), 5.08 (dd, J=14.2, 6.4 Hz, 1H), 5.00 (s, 2H), 4.30 (dd, J=8.3, 6.3 Hz, 1H), 3.76 (s, 3H), 3.70 (t, J=7.8 Hz, 1H), 1.55 (s, 3H), 1.49 (s, 3H); $^{13}$C NMR (CDCl$_3$, 100 MHz): 153.8, 152.6, 138.6, 137.0, 127.5 (2C), 126.2 (2C), 115.7 (2C), 114.5 (2C), 109.6, 77.6, 71.5, 70.3, 55.6, 26.6, 25.9; MS (EI) m/z 314 (M$^+$).

1.4: (1R)-1-[4-[(4-methoxyphenoxy)methyl]phenyl]ethane-1,2-diol ((R)-5) [Sample No, HTKP1-24]

Colorless solid, mp 144° C.; $^1$H NMR (DMSO-d$_6$, 400 MHz): 7.38 (s, 4H), 6.94 (d, J=8.8 Hz, 2H), 6.86 (d, J=8.8 Hz, 2H), 5.32-5.31 (m, 2H), 5.00 (s, 2H), 4.82-4.80 (m, 1H), 4.62-4.61 (m, 1H), 3.68 (s, 3H), 3.55 (brs, 1H), 3.50 (brs, 1H); $^{13}$C NMR (DMSO-d$_6$, 100 MHz): 153.6, 152.5, 143.1, 136.0, 127.4 (2C), 126.5 (2C), 115.8 (2C), 114.7 (2C), 73.8, 69.7, 67.6, 55.4; MS (EI) m/z 274 (M$^+$).

1.5: 2nd-G Dendron of bis(acetonide) ether ((R)-6) [Sample No, HTKP1-63 (2nd fraction)]

Yellow oil; $^1$H NMR (CDCl$_3$, 400 MHz): 7.43-7.24 (m, 12H), 6.92 (d, J=9.3 Hz, 2H), 6.83 (d, J=9.3 Hz, 2H), 5.08-5.04 (m, 2H), 5.00 (s, 2H), 4.63-4.49 (m, 4H), 4.23 (t, J=6.4 Hz, 3H), 3.75 (s, 3H), 3.73-3.66 (m, 4H), 3.55 (dd, J=10.3, 3.9 Hz, 3H), 1.55 (s, 3H), 1.48 (s, 3H); $^{13}$C NMR (CDCl$_3$, 100 MHz): MALDI-TOF-MASS (EI) m/z 571 (M$^+$+Na—H).

1.6: 2nd-G dendron of bis(acetonide) benzyl alcohol ((R)-7) [Sample No, HTKP1-66-4]

Yellow oil; $^1$H NMR (CDCl$_3$, 400 MHz): 7.36-7.21 (m, 12H), 5.08-5.04 (m, 2H), 4.68 (s, 3H), 4.61-4.48 (m, 4H), 4.28 (t, J=6.8 Hz, 3H), 3.75-3.66 (m, 3H), 3.54 (dd, J=10.8, 3.6 Hz, 3H), 3.46 (s, 1H), 1.91 (brs, 1H), 1.55 (s, 3H), 1.48 (s, 3H); $^{13}$C NMR (CDCl$_3$, 100 MHz): 172.8, 169.0, 129.9, 109.2, 60.3, 34.9, 29.4, 25.8, 21.9, 14.2.

1.7: 2nd-G dendron of bis(acetonide) benzyl bromide ((R)-8) [Sample No, HTKP1-67-2]

Colorless oil; $^1$H NMR (CDCl$_3$, 400 MHz): 6.68 (d, J=13.6 Hz, 1H), 5.02-4.92 (m, 1H), 4.14 (q, J=7.2 Hz, 2H), 3.04 (s, 3H), 2.41 (br, 4H), 2.20 (s, 3H), 1.26 (t, J=7.2 Hz, 3H); $^{13}$C NMR (CDCl$_3$, 100 MHz): 172.8, 169.0, 129.9, 109.2, 60.3, 34.9, 29.4, 25.8, 21.9, 14.2.

Example 4

T1 Relaxation Time Measurement of Gd Triamine 2nd G-12-ol-Dendrimer Complex ((R)-11) by 500 MHz NMR (1)

The T1 relaxation time measurement was performed using a broadband probe on a 500 MHz NMR apparatus (Avance 500 manufactured by Bruker Biospin K.K.). The T1 relaxation times were measured at 27° C. using an inversion recovery method.

First, a Gd triamine 2nd G-12-ol-dendrimer complex (R)-11 was dissolved in 1 ml of ultrapure water to prepare an aqueous solution in which the concentration of complex (R)-11 was 24.05 mM. In addition, the concentration of complex (R)-11 was determined from the Gd concentration by inductive coupled plasma emission spectrometry (ICP emission spectrometry). Next, the aqueous solution was diluted with ultrapure water and heavy water so that the concentration of complex (R)-11 was 0.13 mM and the concentration of heavy water was 10%, and the resulting aqueous solution was used as an NMR measurement sample. FIG. 1 shows the T1 time measurement data of water of the prepared sample. The data shown in FIG. 1 clarified that the T1 time of water of the complex (R)-11 aqueous solution was 429 ms.

Comparative Example 1

T1 Relaxation Time Measurement of GdCl$_3$ and Gd (DTPA) (DTPA: Diethylene Triamine Pentaacetic Acid) by NMR (1)

Figure 2:
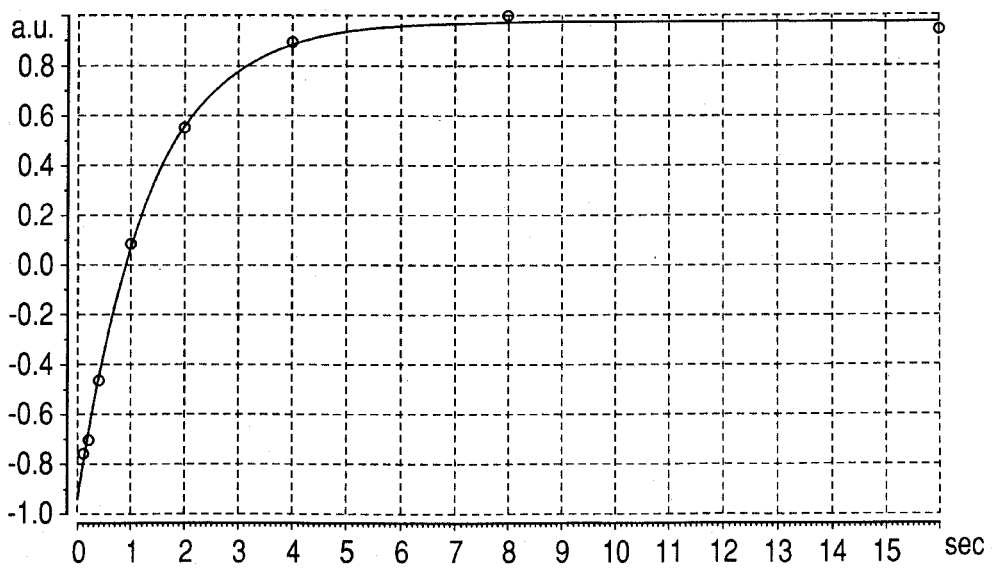
FIG. 2 shows T1 relaxation time measurement data of a sample water prepared by adding 10% heavy water to an aqueous solution of 0.13 mM Gd (DTPA), as measured by using a 500 MHz NMR apparatus in Comparative Example 1.
Figure 3:
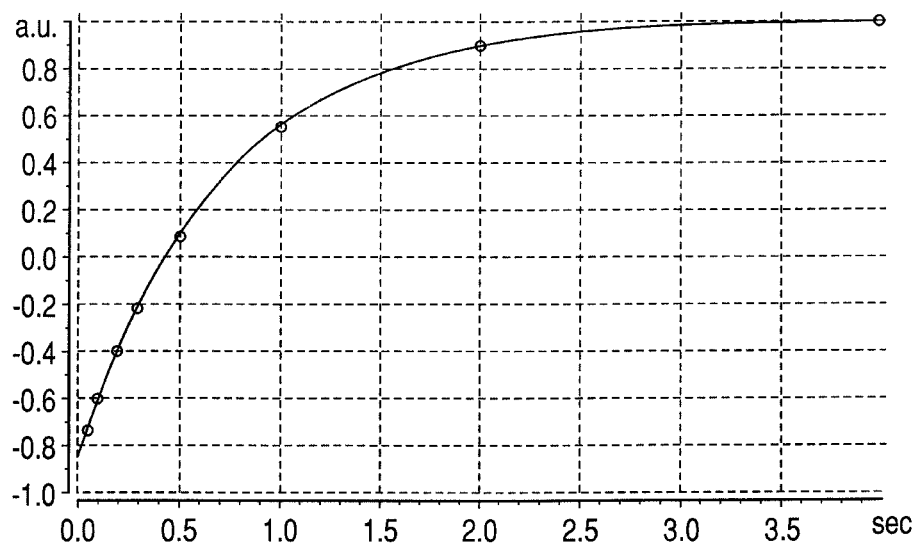
FIG. 3 shows T1 relaxation time measurement data of a sample water prepared by adding 10% heavy water to an aqueous solution of 0.13 mM $GdCl_3$, as measured by using a 500 MHz NMR apparatus in Comparative Example 1.

The T1 relaxation time was measured in the same manner as in Example 4. A GdCl$_3$ aqueous solution was prepared by dissolving commercially available GdCl$_3$.6H$_2$O in ultrapure water and heavy water so that the concentration of GdCl$_3$ was adjusted to 0.13 mM and the concentration of heavy water was adjusted to 10%, and used as an NMR measurement sample. A Gd (DTPA) aqueous solution was prepared by diluting a commercially available Gd (DTPA) aqueous solution (630 mM) with ultrapure water and heavy water so that the concentration of Gd (DTPA) was adjusted to 0.13 mM and the concentration of heavy water was adjusted to 10%, and used as an NMR measurement sample. FIG. 2 shows the T1 time measurement data of water for the Gd (DTPA) aqueous solution sample, and FIG. 3 shows the same data for the GdCl$_3$ aqueous solution sample. The T1 relaxation time of water for the Gd (DTPA) aqueous solution sample determined from the data shown in FIG. 2 was 1333 ms, which is considerably longer than the T1 relaxation time of complex (R)-11. This result suggests that complex (R)-11 of the present invention has considerably greater T1-reducing ability than Gd (DTPA) which is a commercially available MRI contrast agent.

Further, the T1 time of water for the GdCl$_3$ aqueous solution (0.13 mM) determined from the data shown in FIG. 3 was 712 ms, which is greater than the T1 relaxation time of complex (R)-11 shown in Example 4. This suggests that complex (R)-11 has greater T1 relaxation ability than GdCl$_3$. Table 1 summarizes the T1 relaxation time of water for each of the above samples.

TABLE 1

| Sample | Complex (R)-11 0.13 mM | GdCl$_3$ 0.13 mM | Gd (DTPA) 0.13 mM |
|---|---|---|---|
| T1 (ms) | 429 | 712 | 1333 |

Example 5

Figure 4:
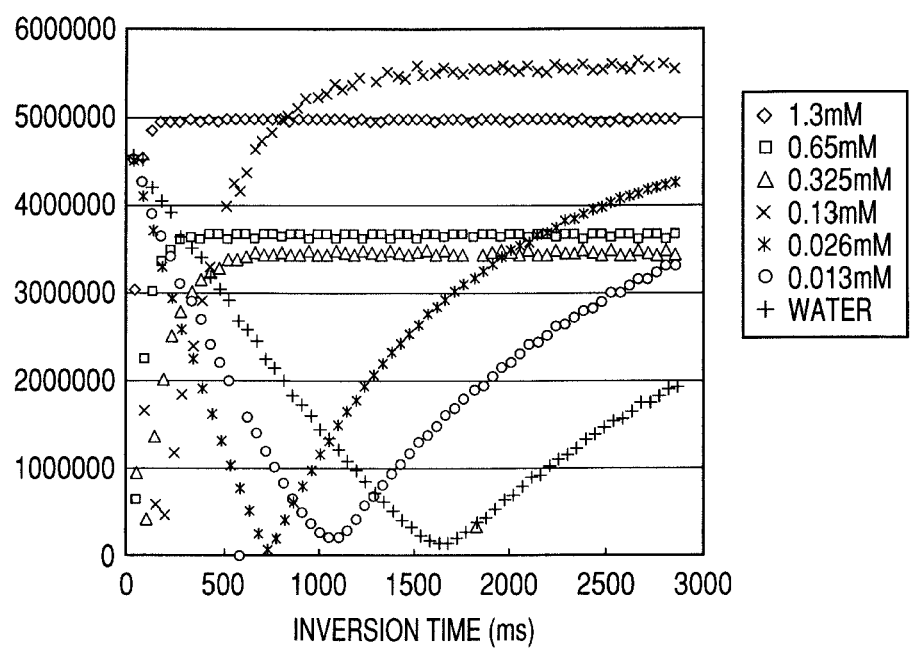
FIG. 4 shows T1 relaxation time measurement data of an aqueous solution of 1.3 mM, 0.65 mM, 0.325 mM, 0.13 mM, 0.026 mM, and 0.013 mM complex (R)-11 and purified water, as measured by a 7T MRI apparatus in Example 5.
Figure 5:
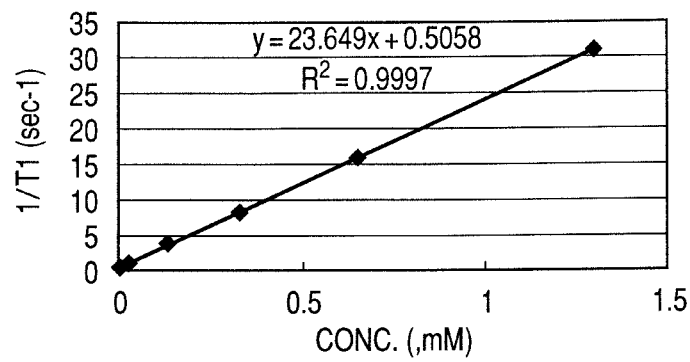
FIG. 5 shows a graph of the relation between the concentration of the complex (R)-11 and 1/T1 in Example 5.

T1 Relaxation Time Measurement of Gd triamine 2nd G-12-ol-dendrimer Complex ((R)-11) by MRI The T1 relaxation time measurement by MRI was performed using a 7T MRI apparatus (BioSpec 70/20 manufactured Bruker Biospin K.K.). The T1 relaxation time was measured under the measurement conditions of TR/TE=3/1.5 ms, FOV=8*4 cm, matrix=128*128, NA=2 and a temperature of 24° C. using an inversion recovery FISP method. Aqueous solutions of six different concentrations (1.3 mM, 0.65 mM, 0.325 mM, 0.13 mM, 0.026 mM and 0.013 mM) were prepared by dissolving complex (R)-11 in ultrapure water, and each of the aqueous solutions was placed into an Eppendorf tube and used directly as a measurement sample. FIG. 4 shows the T1 relaxation time measurement data for complex (R)-11 at each concentration, Table 2 shows the T1 relaxation time and T1 relaxation rate (1/T1) of water at each concentration determined from the T1 relaxation time measurement data, and FIG. 5 shows a graph of the concentration vs 1/T1 of the complex (R)-11. As shown in FIG. 5, 1/T1 and the sample concentration showed an excellent linear relationship. Based on the value of the slope, the T1 relaxation ability of complex (R)-11, r1 was 23.649 (L/mmol·s).

TABLE 2

| | Complex (R)-11 Concentration (mM) | | | | | | |
|---|---|---|---|---|---|---|---|
| | 0 (Water) | 0.013 | 0.026 | 0.13 | 0.325 | 0.65 | 1.3 |
| T1 (ms) | 2377.43 | 1546.8 | 1057.39 | 254.852 | 121.196 | 62.4507 | 32.116 |
| 1/T1 (s$^{-1}$) | 0.420622 | 0.646496 | 0.945725 | 3.923846 | 8.251097 | 16.01263 | 31.13713 |

Comparative Example 2

Figure 6:
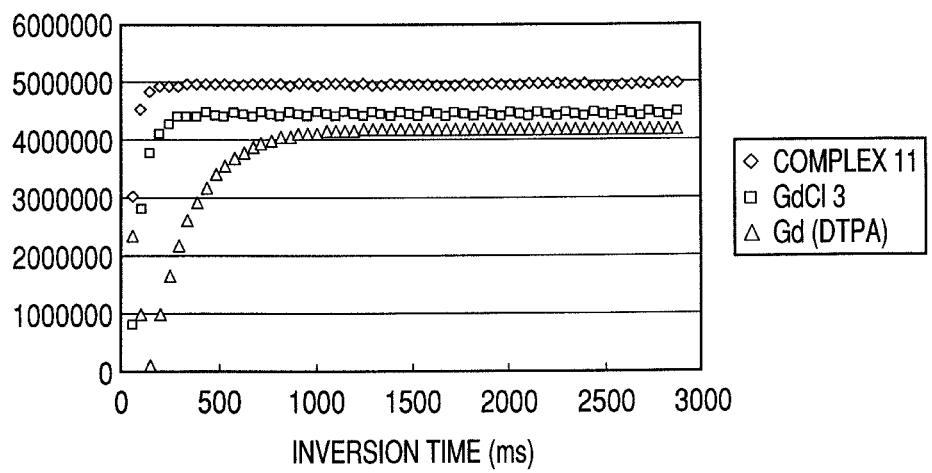
FIG. 6 shows T1 relaxation time measurement data of water for an aqueous solution of 1.3 mM GdCl$_3$ and an aqueous solution of 1.3 mM Gd (DTPA), as measured by a 7T MRI apparatus in Comparative Example 2.

T1 Relaxation Time Measurement of GdCl$_3$ and Gd (DTPA) (DTPA: Diethylene Triamine Pentaacetic Acid) by MRI The T1 relaxation time was measured in the same manner as in Example 5. A GdCl$_3$ aqueous solution was prepared by dissolving commercially available GdCl$_3$·6H$_2$O in ultrapure water so that the concentration was adjusted to 1.3 mM, and Gd (DTPA) aqueous solutions were prepared by diluting a commercially available Gd (DTPA) aqueous solution (630 mM) with ultrapure water so that the concentration was adjusted to 2.0, 1.3, 1.0, 0.5 and 0.25 mM, respectively. Each of the aqueous solutions was placed into an Eppendorf tube and used directly as a measurement sample. FIG. 6 shows the results of the T1 relaxation time measurement for the GdCl$_3$ aqueous solution (1.3 mM) and Gd (DTPA) aqueous solution (1.3 mM), and Table 3 shows a summary of the T1 relaxation time determined from the results. The T1 relaxation time of water for the Gd (DTPA) aqueous solution was 205.653 ms, which is a considerably longer than the T1 relaxation time (32.116 ms) of water for complex (R)-11 at the same concentration as determined in Example 5.

TABLE 3

| Sample | Complex (R)-11 1.3 mM | Gd (DTPA) 1.3 mM | GdCl$_3$ 1.3 mM |
|---|---|---|---|
| T1 (ms) | 32.116 | 205.653 | 58.991 |

Figure 7:
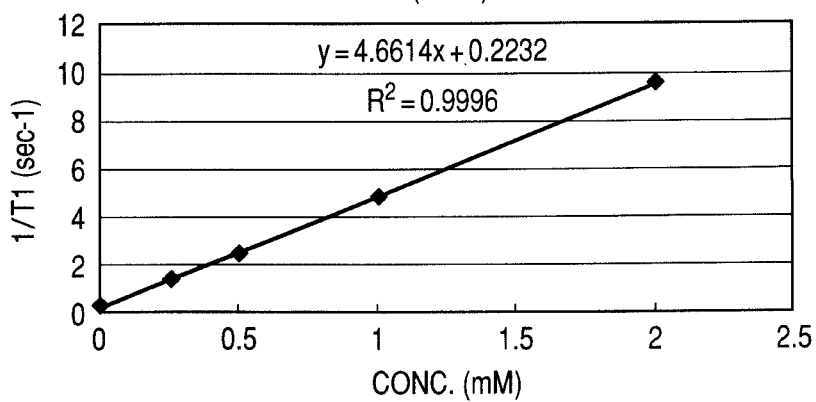
FIG. 7 shows a graph of the relation of the concentration between the Gd (DTPA) and 1/T1 in Comparative Example 2.

Further, as a comparison, the T1 relaxation ability was determined at 24° C. using Gd (DTPA) aqueous solutions of 2.0, 1.0, 0.5 and 0.25 mM by a saturation recovery spin echo method, and as a result r1 was 4.661 (L/mmol·s) (FIG. 7). The r1 of Gd (DTPA) was approximately one-fifth of the r1 (23.649 (L/mmol·s)) of complex (R)-11 determined in Example 5, and it was clear that complex (R)-11 of the present invention had a T1-reducing ability that was about five-fold higher than that of the MRI contrast agent Gd (DTPA), which is currently commercially available.

In addition, the T1 relaxation time of water for the GdCl$_3$ aqueous solution (1.3 mM) was 58.991 ms, which is slightly longer than the T1 relaxation time of complex (R)-11 (1.3 mM) shown in Example 5. Therefore, complex (R)-11 has a slightly greater T1 relaxation ability than GdCl$_3$.

Figure 8:
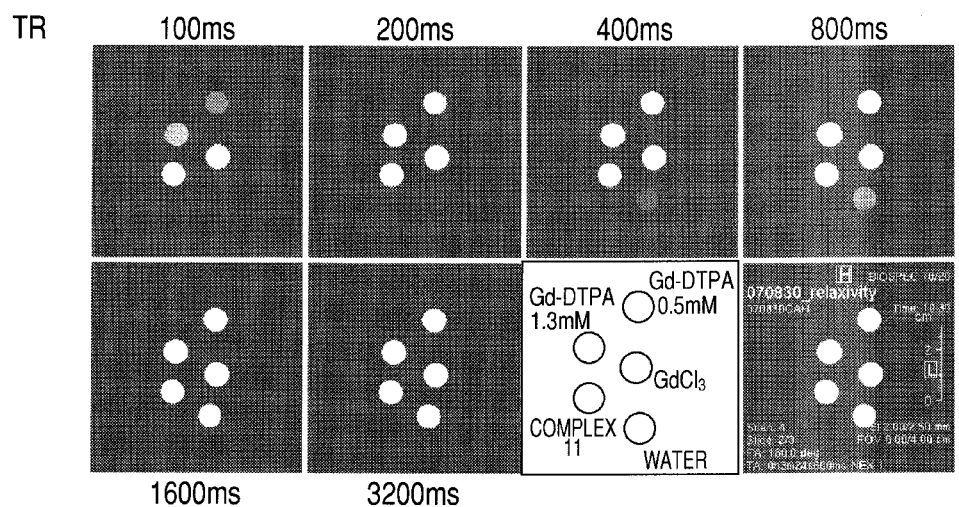
FIG. 8 shows an MRI image of a phantom of an aqueous solution of complex (R)-11 (1.3 mM), GdCl$_3$ (1.3 mM) and Gd (DTPA) (1.3 and 0.5 mM) and water, as measured by changing the TR using 7T MRI apparatus.

FIG. 8 shows MRI images of each sample (complex (R)-11 (1.3 mM), GdCl$_3$ (1.3 m), Gd (DTPA) (1.3 and 0.5 mM) and water) obtained by a saturation recovery spin echo method. Even in the actual MRI image, especially where TR is in the vicinity of 100 to 400 ms, the complex (R)-11 gives a greater contrast than Gd (DTPA). Therefore, complex (R)-11 of the present invention has a high T1 relaxation ability that is superior to that of a commercially available contrast agent as a positive MRI contrast agent.

Example 6

Mouse MRI Contrast Imaging Experiment with Gd triamine 2nd Generation-12-ol-dendrimer Complex (11)

The contrast imaging of a mouse by MRI was performed by using a circularly polarized RF resonator with an internal diameter of 72 mm manufactured by Bruker Biospin K.K. on a 7T MRI apparatus (BioSpec 70/20 manufactured by Bruker Biospin K.K.). T$_1$-weighted images were taken before and after the administration of a contrast agent using male C57/BL6 mice (21 to 24 g, 8 weeks age) under 1 to 1.5% isoflurane anesthesia. The administration of the contrast agent was administered by administering complex (R)-11 prepared so that the Gd concentration was 1 mmol/L in the mouse tail vein. During the administration period, no acute toxicity caused by the administration was observed.

In addition, the MRI T$_1$-weighted images of the mice were obtained under the measurement conditions of TR/TE=200/6.2 ms, NEX=2, FOV=8*4 cm, slice thickness=2 mm and matrix=256*256 using a spin echo method.

Figure 9A:
FIGS. 9A and 9B shows MRI images of a mouse as measured by using a 7T MRI apparatus in Example 6.
Figure 9B:

After the measurement of each MRI image, the signal strength of each organ was measured to compare the signal strength between before and after the administration of a contrast agent. FIG. 9A shows the $T_1$-weighted image of the mouse before the administration of complex (R)-11 and FIG. 9B shows the $T_1$-weighted image of the mouse after the administration of complex (R)-11. As seen in FIG. 9B, a high contrast was obtained, especially in the liver site (near the center of the image).

Example 7

T1 Relaxation Time Measurement of Gd Triamine 2nd Generation-12-ol-Dendrimer Complex ((R)-11) by 500 MHz NMR (2)

The T1 time was measured in the same manner as in Example 4 except that the NMR measurement sample was changed to an FBS (fetal bovine serum) solution of the complex (R)-11 (FBS concentration: 80%, heavy water concentration: 10%, $H_2O$ concentration: 10%).
As a result, the T1 time of water for the FBS solution of the complex (R)-11 was 1135 ms.

Comparative Example 3

T1 Relaxation Time Measurement of $GdCl_3$ and Gd (DTPA) (DTPA: Diethylene Triamine Pentaacetic Acid) by 500 MHz NMR (2)

The T1 time was measured in the same manner as in Comparative Example 1 except that the NMR measurement sample was changed to an FBS (fetal bovine serum) solution of $GdCl_3$ or Gd (DTPA) (FBS concentration: 80%, heavy water concentration: 10%, $H_2O$ concentration: 10%).
As a result, the T1 relaxation time of water for the Gd (DTPA) FBS solution was 1429 ms, and the T1 time of water for the $GdCl_3$ FBS solution was 1708 ms.
From the above results, it became clear that the T1 relaxation ability of $GdCl_3$ was significantly decreased in an FBS solution which is close to that in a living body, and the T1 relaxation ability of complex (R)-11 was decreased in an FBS solution which is close to that in living body, but was still greater than that of Gd (DTPA).

Example 8

XAFS Measurement and Analysis of Gd Triamine 2nd Generation-12-ol-dendrimer Complex ((R)-11)

The XAFS analysis of the complex (R)-11 was performed at Spring-8.
Specifically, the number of the coordinated water molecules was estimated by removing background from XAFS spectra and performing fitting using Fourier transformation or Fourier inverse transformation.
Further, the XAFS spectra were obtained by a transmission method using an ion chamber for a pellet (in a powder state) of the complex ((R)-11) and a fluorescence method using a multi-element semiconductor detector for an aqueous solution of the complex ((R)-11), respectively.
When fitting was performed without fixing the proximal coordination number to 9, the following results were obtained. In a powder state, the coordination number of O was 6.99 and the distance between atoms of Gd and O was 2.421 Å, and in an aqueous solution (3 mM) the coordination number of O was 9.77 and the distance between atoms of Gd and O was 2.430 Å. In the measurement results, it is presumed that most of the coordinated oxygen atoms are derived from water because no carbon atoms were observed in the second coordination sphere and the atomic distance was too short if a hydroxyl group was coordinated.
For comparison purpose, the XAFS analysis was performed for Gd (DTPA) and Gd (DOTA), and the coordination number of water molecule was 1.
Therefore, although the accurate number of water molecules was not clear, it was confirmed that the number of water molecules coordinated to the complex ((R)-11) was considerably larger than that of Gd (DTPA) and Gd (DOTA), which are existing contrast agents.

Example 9

1. Synthesis of 2nd Generation-Chiral-Acetonide Tetraamine Dendrimer (R)-9a

Figure 10A:
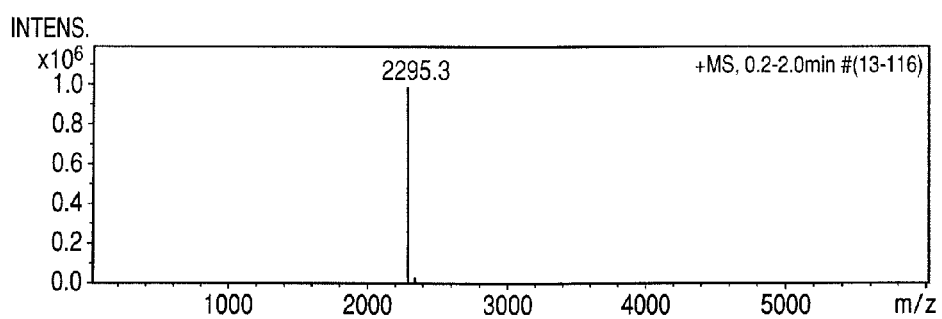
FIGS. 10A and 10B shows ESI-TOS MS spectra of the 2nd Generation-chiral-acetonide tetraamine dendrimer (R)-9a synthesized in Example 9.
Figure 10B:
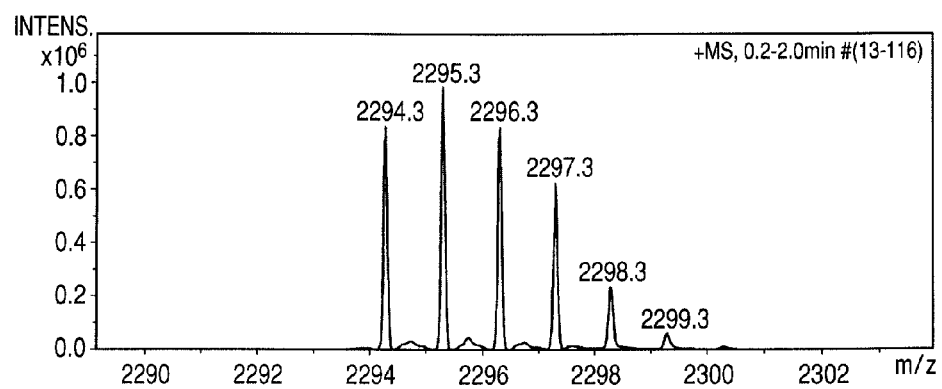

A 2nd Generation-chiral acetonide tetraamine dendrimer (R)-9a, which differs from (R)-9 only in the core site, was synthesized in the same manner as in Example 2 except that 1,4,7,10-tetraazacyclododecane was used instead of TACN as a raw material of the core site.
FIG. 10A and FIG. 10B show the ESI-TOS MS spectra.

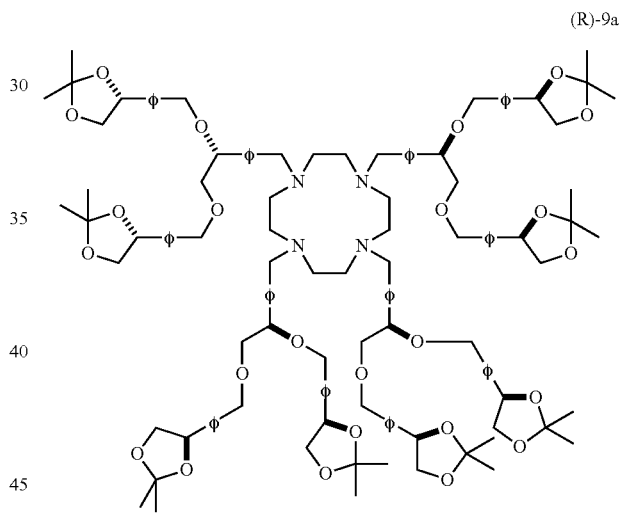

(R)-9a

2. Synthesis of 2nd Generation-chiral-16-ol-tetraamine Dendrimer (R)-10a

A 2nd Generation-chiral-16-ol-tetraamine dendrimer (R)-10a was obtained by hydrolyzing (R)-9a in the same manner as in Example 2.

Example 10

Synthesis of 2nd Generation-chiral-12-ol-tetraamine Dendrimer Gadolinium Complex (R)-11a A 2nd Generation-chiral-12-ol-tetraamine dendrimer gadolinium Complex (R)-11a was obtained by coordinating the 2nd Generation-chiral-12-ol-tetraamine dendrimer (R)-10a to Gd in the same manner as in Example 3.

Example 11

T1 Relaxation Time Measurement of 2nd Generation-chiral-16-ol-tetraamine dendrimer gadolinium Complex (R)-11a by MRI The T1 relaxation time of complex (R)-11a was measured by 7T MRI in the same manner as in Example 4.

As a result, the T1 relaxation ability of the complex (R)-11a, r1, was shown to be 8.4 (L/mmol·s).

As mentioned above, according to the present invention, there may be provided a metal complex which exhibits a T1-reducing effect superior to that of a conventional compound and an MRI contrast agent containing the metal complex.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-309087, filed Nov. 29, 2007, and Japanese Patent Application No. 2008-040990, filed Feb. 22, 2008, which are hereby incorporated by reference herein in their entirety.

The invention claimed is:

1. A metal complex compound represented by formula (1), which is coordinated to a metal ion selected from the group consisting of a lanthanoid ion, a manganese ion, a chromium ion, and an iron ion:

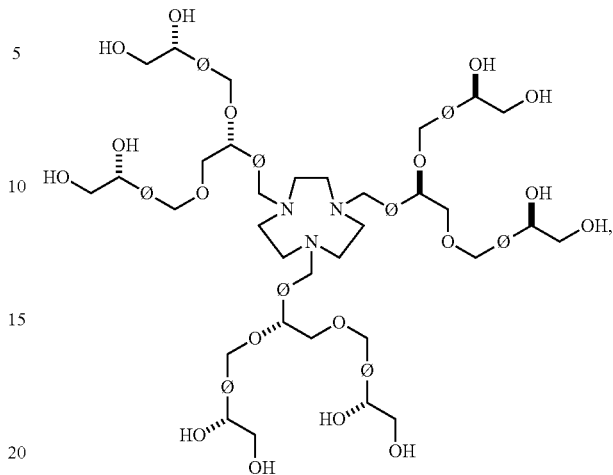

(1)

wherein φ represents a phenylene group.

2. The metal complex compound according to claim 1, wherein the metal ion is a gadolinium ion.

3. The metal complex compound according to claim 1, which comprises a chloride ion as a counter ion.

* * * * *